US009102967B2

(12) United States Patent
Chen et al.

(10) Patent No.: US 9,102,967 B2
(45) Date of Patent: Aug. 11, 2015

(54) PMST2 ENZYME FOR CHEMOENZYMATIC SYNTHESIS OF α-2-3-SIALYLGLYCOLIPIDS

(71) Applicant: The Regents of the University of California, Oakland, CA (US)

(72) Inventors: Xi Chen, Woodland, CA (US); Vireak Thon, San Francisco, CA (US); Kam Lau, Queensland (AU)

(73) Assignee: The Regents of the University of California, Oakland, CA (US)

( * ) Notice: Subject to any disclaimer, the term of this patent is extended or adjusted under 35 U.S.C. 154(b) by 157 days.

(21) Appl. No.: 13/739,705

(22) Filed: Jan. 11, 2013

(65) Prior Publication Data
US 2013/0196385 A1 Aug. 1, 2013

Related U.S. Application Data

(60) Provisional application No. 61/585,376, filed on Jan. 11, 2012.

(51) Int. Cl.
*C12N 9/10* (2006.01)
*C12P 19/18* (2006.01)
*C12P 19/44* (2006.01)

(52) U.S. Cl.
CPC .............. *C12P 19/18* (2013.01); *C12N 9/1081* (2013.01); *C12P 19/44* (2013.01); *C07K 2319/21* (2013.01); *C07K 2319/24* (2013.01)

(58) Field of Classification Search
CPC ....................... C12N 9/01–9/81; C12N 9/1081
USPC ......................................................... 435/193
See application file for complete search history.

(56) References Cited

U.S. PATENT DOCUMENTS

| 5,374,541 | A | 12/1994 | Wong et al. |
| 2005/0089956 | A1* | 4/2005 | Endo et al. ................... 435/69.1 |
| 2007/0275908 | A1 | 11/2007 | Defrees et al. |
| 2009/0215115 | A1 | 8/2009 | Gilbert et al. |
| 2010/0291631 | A1 | 11/2010 | Yamamoto et al. |

OTHER PUBLICATIONS

Thon et al. 2011; PmST2: A novel Pasteruella multocida glycolipid alpha 2-3-sialultransferase. Glycobiology. 21(9): 1206-1216.*
Audry et al. available Nov. 2010; Current trends in the structure-activity relationships of sialyltransferases. Glycobiology 21(6): 716-726.*
Audry et al., "Current trends inthe structure-activity relationships of sialyltransferases," Glycobiology, 2011, vol. 21(6), pp. 716-726.
Cheng et al., "Multifunctionality of Campylobacter jejuni sialyltransferase Cstll: Characterizatiion of GD3/GT3 oligosaccharide synthase, GD3 oligosaccharide sialidase, and trans-sialidase activites," Glycobiology, 2008, vol. 18(9), pp. 686-697.
Chung et al., "Vaccination against fowl cholera with acapsular *Pasteurella multocida* A:1," Vaccine, 2005, 23: 2751-2755.

Coutinho et al., "An evolving hierarchical family classification for glycosyltransferases," J Mol Biol., 2003, vol. 328, pp. 307-317.
Gilbert et al., "Characterization of a recombinant *Neisseria meningitides* alpha-2,3-sialyltransferase and its acceptor specificity," Eur J Biochem., 1997, 249: 187-194.
Gilbert et al., "Cloning of the lipooligosaccharide alpha-2,3-sialyltransferase from the bacterial pathogens *Neisseria meningitidis* and *Neisseria gonorrhoeae*," J Biol Chem., 1996, 271:28271-28276.
Izumi et al., "Microbial glycosyltransferases for carbohydrate synthesis: Alpha-2,3-sialyltransferase from *Neisseria gonorrheae*," J Am Chem Soc., 2001, 123:10909-10918.
Kakuta et al., "Crystal structure of *Vibrionaceae hotobacterium* sp. JT-ISH-224 α2,6-sialyltransferase in a ternary complex with donor product CMP and acceptor substrate lactose: catalytic mechanism and substrate recognition," Glycobiology, 2008, vol. 18(1), pp. 66-73.
Kim et al., "Structural analysis of sialyltransferase PM0188 from *Pasteurella multocida* complexed with donor analogue and acceptor sugar," BMB Reports, 2008, vol. 41(1), pp. 48-54.
Kushi et al., "Sialyltransferases of marine bacteria efficiently utilize glycosphingolipid substrates," Glycobiology, 2010, 20:187-198.
Lairson et al., "Glycosyltransferases: Structures, Functions, and Mechanisms," Annu. Rev. Biochem., 2008, vol. 77, pp. 521-555.
Larsson et al., "Synthesis of reference standards to enable single cell metabolomic studies of tetramethylrhodaminelabeled ganglioside GM1," Carbohydr Res., 2007, 342:482-489.
Li et al., "The Hd0053 gene of *Haemophilus ducreyi* encodes an alpha2,3-sialyltransferase," Biochem Biophys Res Commun, 2007, vol. 361(2), pp. 555-560.
Li et al., "Sialic acid metabolism and sialyltransferases: natural functions and applications," Appl. Microbiol. Biotechnol., 2012, vol. 94, pp. 887-905.
Liu et al., "A striking example of the interfacing of glycal chemistry with enzymatically mediated sialylation: A concise synthesis of ganglioside GM3," J Am Chem Soc., 1993, 115:4933-4934.
May et al., "Complete genomic sequence of *Pasteurella multocida*, Pm70," Proc Natl Acad Sci USA, 2001, 98:3460-3465.
Ni et al., "Cytidine 5'—monophosphate (CMP)-induced structural changes in a multifunctional sialyltransferase from *Pasteurella multocida*," Biochemistry, 2006, 45:2139-2148.
Nishimura et al., "Transfer of ganglioside GM3 oligosaccharide from a water soluble polymer to ceramide by ceramide glycanase. A novel approach for the chemical-enzymatic synthesis of glycosphingolipids," J Am Chem Soc., 1997, 119:10555-10556.
Steenbergen et al., "Sialic acid metabolism and systemic pasteurellosis," Infect Immun., 2005, 73:1284-1294.
St Michael et al., "Structural analysis of the lipopolysaccharide from *Pasteurella multocida* genome strain Pm70 and identification of the putative lipopolysaccharide glycosyltransferases," Glycobiology, 2005, 15:323-333.

(Continued)

*Primary Examiner* — Karen Cochrane Carlson
(74) *Attorney, Agent, or Firm* — Kilpatrick Townsend & Stockton LLP

(57) ABSTRACT

The present invention provides novel methods for preparing glycolipid products. Novel sialyltransferases are also disclosed.

13 Claims, 6 Drawing Sheets

(56) References Cited

OTHER PUBLICATIONS

Yu et al., "A multifunctional *Pasteurella multocida* sialyltransferase: A powerful tool for the synthesis of sialoside libraries,” J Am Chem Soc., 2005, 127:17618-17619.

Zehavi et al., “Enzymic glycosphingolipid synthesis on polymer supports. III. Synthesis of G(M3), its analog [NeuNAc alpha(2-3) Gal beta(1-4)Glc beta(1-3)Cer] and their lyso-derivatives,” Glycoconjugate J., 1998, 15:657-662.

* cited by examiner

Figure 1

```
                                                                                                *
PmST2   : ------------------------------------------MN LI  CC T  LQ :  11
HiLsgB  : ------------------------------------------MN LI  CC T  LQ :  11
NmLst   : M GL KK AC LT V LC LI VF CF GI F YT FD RV NQ GE R NA VS LL KE KL F NE EG EP VN LI F CY TI LQ :  60

PmST2   : V  I A  KI I  K FP HT P  YG VM  ST  S N  K   Y  K  L  Q   G F  S  V QH  R- - -F NL L  :  68
HiLsgB  : V  I AR KI IE L  P N  F F  VM F GR  W D  KR TL Y  S  L   V  SD S MN  D TG   K G -F D  L  :  70
NmLst   : M KV A  RI M  Q  P G  RF YV VL   E NR NE K    Y FN Q  KD KA  R A  F FH LP YG  N K S F N   P : 120

PmST2   : E IL YL KR T- F SG  H  D  V FV A NI  D  Q I  FL  SA  D  N LL NT F DD GT IN I   N  L  YQ  D : 127
HiLsgB  : L MR  L KN  -  SH  G   V FLA  L  S W  Q    SH  S  K  L YT F DD GS DN IF  H P NL  R E- : 128
NmLst   : T MA   L KV  S   LL PK VK  I YLA S  EK  S  IA A  L ST YP DA  I KT F DD GT GN L   QS  S      G  E : 180

PmST2   : --- A T   Q       NV  L G   Y S IQ S   A L  HT  I YT IY   K NI I ER --     EL V AA  N    : 182
HiLsgB  : ---  D TF  Y     A FI G   Y S VN   FK KI KK H YT VY PN   K NI V S   --    S L W DN QI DC : 183
NmLst   : F SV NG T    N FA  R    I C- D W S IA  T  N A  DE H YT IF   LK NI M  GR RK MT Y  P LF  A    : 239

PmST2   : K    SA  I NV L  G   VF AE  D R N  AL A  R  I   N  H Y   P HP  EK Y  LA Q V   I T -  I   : 242
HiLsgB  : E  D  E   S -F F  G   LL NT K   D   SL IK K  KE   S FD Y   P HP A  ED Y  VD  V    V ES    I   : 242
NmLst   : L K   D E   GG T VR IL LG SP  K  MK E  S  RA A  N  K  Q YV AP HP   T YG LS  V TT L  S PY V I : 299

PmST2   : E DY I   Q   CQ T -- -H   C V YT Y FS  A  I  I  N K SD NI  V V  LK I D- -   A   D A  Y    D : 297
HiLsgB  : E DY VF  Y  S N --- K II I  Y T F FS  V F  L  S H - NV  I RF IR- --- -  SI R  Q F  Y  S  P : 294
NmLst   : E DY I      K K NP HT   Y EI YT F FS G   A  TM K  F  - NV  V Y  LK P AS LP   YW LK P V Y A   T : 358

PmST2   :   G VN V  DI R E- - : 308
HiLsgB  : D  G IK  Y KE I --- : 304
NmLst   :   SG IP I  TF D DK N : 371
```

Figure 4
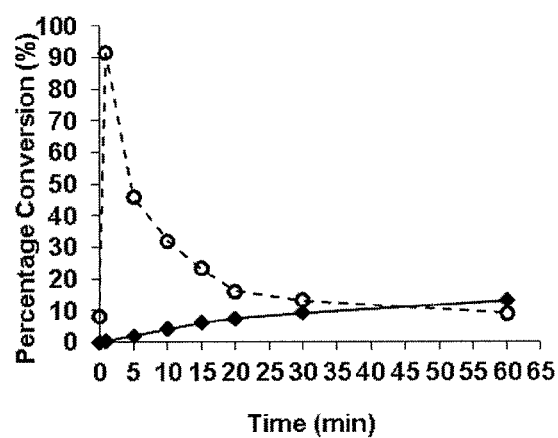
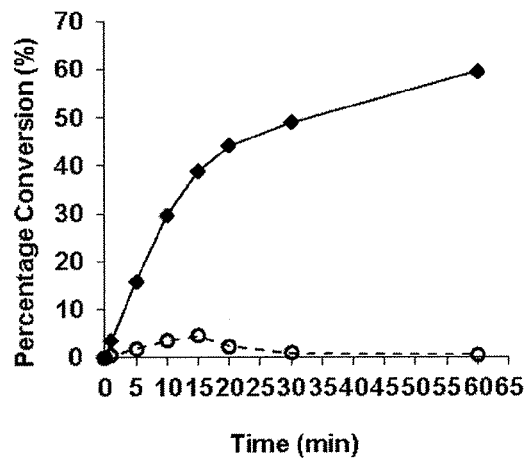

Figure 8, cont.
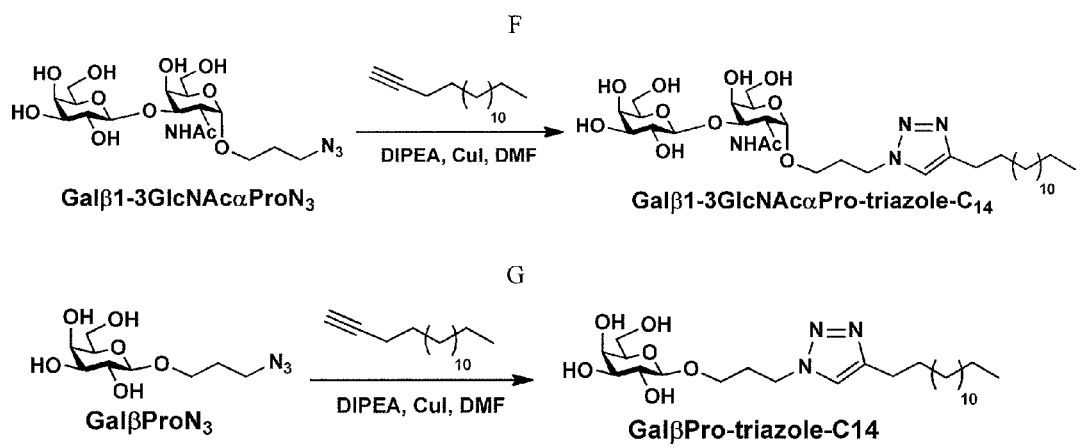

SEQUENCE LISTING

```
<160> NUMBER OF SEQ ID NOS: 15

<210> SEQ ID NO 1
<211> LENGTH: 927
<212> TYPE: DNA
<213> ORGANISM: Pasteurella multocida
<220> FEATURE:
<223> OTHER INFORMATION: Pasteurella multocida strain P-1059
      (ATCC 15742) Pm0508 homolog sialidase-free monofunctional
      alpha-2,3-sialyltransferase

<400> SEQUENCE: 1
atgaatttga ttatttgttg tacaccgtta caggtgttga ttgcagaaaa aattatcgct      60
aaatttccgc atacgccatt ttatggtgtc atgctttcaa cagtcagtaa taaaaaattt     120
gatttttatg caaagcggct tgcgcaacag tgccaaggtt ttttttccat ggtgcagcat     180
aaggatcgct tcaatctatt aaaagaaatt ctgtatttaa aacgaacatt ttcgggtaag     240
cactttgatc aggtttttgt ggcaaacatt aatgacttac aaattcagtt tttattaagt     300
gccattgact ttaatctgtt aaataccttt gatgacggca caattaatat tgtaccgaat     360 agtcttttt accaagatga ccctgccacg ttgcagcgaa aactgattaa tgtgctgtta     420
ggtaataaat acagtattca atcattacgc gctttatccc atacacacta cactatttat     480
aaaggcttca agaatattat tgaacgggta gagccgattg aattggtcgc agcagataac     540
agtgaaaaag tcacttcagc ggtgattaac gtattgcttg gcaacccgt ttttgctgaa     600 gatgaacgca atattgcctt agcggaacgc gtgatcaaac aatttaatat tcattattat     660
```

```
ttgcctcatc cacgcgaaaa gtatcgttta gcccaagtca attacattga tacggaattg    720
atctttgaag attatattct tcagcaatgt caaacccaca atactgtgt ttatacatat     780 tttagtagcg ccattattaa tatcatgaat aaaagtgaca atattgaagt ggtagcatta   840
aaaattgaca cagaaaatcc cgcctacgat gcttgttatg atttgtttga tgagctaggc   900
gttaacgtta ttgatataag agagtaa                                        927
```

<210> SEQ ID NO 2
<211> LENGTH: 1044
<212> TYPE: DNA
<213> ORGANISM: Artificial Sequence
<220> FEATURE:
<223> OTHER INFORMATION: synthetic Pasteurella multocida strain P-1059
( -continued

```
accccggaca aagcgttcca ggacaagctg tatccgttta cctgggatgc cgtacgttac    300
aacggcaagc tgattgctta cccgatcgct gttgaagcgt tatcgctgat ttataacaaa    360
gatctgctgc cgaacccgcc aaaaacctgg gaagagatcc cggcgctgga taaagaactg    420
aaagcgaaag gtaagagcgc gctgatgttc aacctgcaag aaccgtactt cacctggccg    480
ctgattgctg ctgacggggg ttatgcgttc aagtatgaaa acggcaagta cgacattaaa    540
gacgtgggcg tggataacgc tggcgcgaaa gcgggtctga ccttcctggt tgacctgatt    600
aaaaacaaac acatgaatgc agacaccgat tactccatcg cagaagctgc ctttaataaa    660
ggcgaaacag cgatgaccat caacggcccg tgggcatggt ccaacatcga caccagcaaa    720
gtgaattatg gtgtaacggt actgccgacc ttcaagggtc aaccatccaa accgttcgtt    780
ggcgtgctga gcgcaggtat taacgccgcc agtccgaaca aagagctggc aaaagagttc    840
ctcgaaaact atctgctgac tgatgaaggt ctggaagcgg ttaataaaga caaaccgctg    900
ggtgccgtag cgctgaagtc ttacgaggaa gagttggtga aagatccgcg gattgccgcc    960
actatggaaa acgcccagaa aggtgaaatc atgccgaaca tcccgcagat gtccgctttc   1020
tggtatgccg tgcgtactgc ggtgatcaac gccgccagcg gtcgtcagac tgtcgatgaa   1080
gccctgaaag acgcgcagac taattcgagc tcgaacaaca acaacaataa caataacaac   1140
aacctcggga tcgagggaag gatttcagaa ttcatgaatt tgattatttg ttgtacaccg   1200
ttacaggtgt tgattgcaga aaaaattatc gctaaatttc cgcatacgcc attttatggt   1260
gtcatgcttt caacagtcag taataaaaaa tttgattttt atgcaaagcg gcttgcgcaa   1320
cagtgccaag gtttttttc catggtgcag cataaggatc gcttcaatct attaaaagaa    1380
attctgtatt taaaacgaac attttcgggt aagcactttg atcaggtttt tgtggcaaac   1440
attaatgact tacaaattca gtttttatta agtgccattg actttaatct gttaaatacc   1500
tttgatgacg gcacaattaa tattgtaccg aatagtcttt tttaccaaga tgaccctgcc   1560
acgttgcagc gaaaactgat taatgtgctg ttaggtaata aatacagtat tcaatcatta   1620
cgcgctttat cccatacaca ctacactatt tataaaggct tcaagaatat tattgaacgg   1680
gtagagccga ttgaattggt cgcagcagat aacagtgaaa aagtcacttc agcggtgatt   1740
aacgtattgc ttgggcaacc cgtttttgct gaagatgaac gcaatattgc cttagcggaa   1800
cgcgtgatca aacaatttaa tattcattat tatttgcctc atccacgcga aaagtatcgt   1860
ttagcccaag tcaattacat tgatacggaa ttgatctttg aagattatat tcttcagcaa   1920
tgtcaaaccc acaaatactg tgtttataca tattttagta gcgccattat taatatcatg   1980
aataaaagtg acaatattga agtggtagca ttaaaaattg acacagaaaa tcccgcctac   2040
gatgcttgtt atgatttgtt tgatgagcta ggcgttaacg ttattgatat aagagagaag   2100
cttcaccacc accaccacca ctaa                                           2124
```

```

<210> SEQ ID NO 4
<211> LENGTH: 308
<212> TYPE: PRT
<213> ORGANISM: Pasteurella multocida
<220> FEATURE:
<223> OTHER INFORMATION: Pasteurella multocida strain P-1059
      (ATCC 15742) Pm0508 homolog sialidase-free monofunctional alpha-2,
      3-sialyltransferase
<220> FEATURE:
<221> NAME/KEY: HELIX
<222> LOCATION: (1)...(19)
<223> OTHER INFORMATION: transmembrane helix shared among all GT52
      family sialyltransferases
```

<220> FEATURE:
<221> NAME/KEY: HELIX
<222> LOCATION: (85)...(107)
<223> OTHER INFORMATION: transmembrane helix shared among some GT52
      family sialyltransferases

<400> SEQUENCE: 4

Met Asn Leu Ile Ile Cys Cys Thr Pro Leu Gln Val Leu Ile Ala Glu
 1               5                  10                  15

Lys Ile Ile Ala Lys Phe Pro His Thr Pro Phe Tyr Gly Val Met Leu
            20                  25                  30

Ser Thr Val Ser Asn Lys Lys Phe Asp Phe Tyr Ala Lys Arg Leu Ala
        35                  40                  45

Gln Gln Cys Gln Gly Phe Phe Ser Met Val Gln His Lys Asp Arg Phe
    50                  55                  60

Asn Leu Leu Lys Glu Ile Leu Tyr Leu Lys Arg Thr Phe Ser Gly Lys
65                  70                  75                  80

His Phe Asp Gln Val Phe Val Ala Asn Ile Asn Asp Leu Gln Ile Gln
                85                  90                  95

Phe Leu Leu Ser Ala Ile Asp Phe Asn Leu Leu Asn Thr Phe Asp Asp
            100                 105                 110

Gly Thr Ile Asn Ile Val Pro Asn Ser Leu Phe Tyr Gln Asp Asp Pro
        115                 120                 125

Ala Thr Leu Gln Arg Lys Leu Ile Asn Val Leu Leu Gly Asn Lys Tyr
    130                 135                 140

Ser Ile Gln Ser Leu Arg Ala Leu Ser His Thr His Tyr Thr Ile Tyr
145                 150                 155                 160

Lys Gly Phe Lys Asn Ile Ile Glu Arg Val Glu Pro Ile Glu Leu Val
                165                 170                 175

Ala Ala Asp Asn Ser Glu Lys Val Thr Ser Ala Val Ile Asn Val Leu
            180                 185                 190

Leu Gly Gln Pro Val Phe Ala Glu Asp Glu Arg Asn Ile Ala Leu Ala
        195                 200                 205

Glu Arg Val Ile Lys Gln Phe Asn Ile His Tyr Tyr Leu Pro His Pro
    210                 215                 220

Arg Glu Lys Tyr Arg Leu Ala Gln Val Asn Tyr Ile Asp Thr Glu Leu
225                 230                 235                 240

Ile Phe Glu Asp Tyr Ile Leu Gln Gln Cys Gln Thr His Lys Tyr Cys
                245                 250                 255

Val Tyr Thr Tyr Phe Ser Ser Ala Ile Ile Asn Ile Met Asn Lys Ser
            260                 265                 270

Asp Asn Ile Glu Val Val Ala Leu Lys Ile Asp Thr Glu Asn Pro Ala
        275                 280                 285

Tyr Asp Ala Cys Tyr Asp Leu Phe Asp Glu Leu Gly Val Asn Val Ile
    290                 295                 300

Asp Ile Arg Glu
305

<210> SEQ ID NO 5
<211> LENGTH: 347
<212> TYPE: PRT
<213> ORGANISM: Artificial Sequence
<220> FEATURE:
<223> OTHER INFORMATION: synthetic Pasteurella multocida strain P-1059
      (ATCC 15742) Pm0508 homolog sialidase-free monofunctional alpha-2, 3-sialyltransferase C-terminal His-6 tagged fusion protein PmST2-His-6

```
<400> SEQUENCE: 5

Met Lys Tyr Leu Leu Pro Thr Ala Ala Ala Gly Leu Leu Leu Leu Ala
  1               5                  10                  15

Ala Gln Pro Ala Met Ala Met Asp Ile Gly Ile Asn Ser Asp Pro Met
             20                  25                  30

Asn Leu Ile Ile Cys Cys Thr Pro Leu Gln Val Leu Ile Ala Glu Lys
         35                  40                  45

Ile Ile Ala Lys Phe Pro His Thr Pro Phe Tyr Gly Val Met Leu Ser
     50                  55                  60

Thr Val Ser Asn Lys Lys Phe Asp Phe Tyr Ala Lys Arg Leu Ala Gln
 65                  70                  75                  80

Gln Cys Gln Gly Phe Phe Ser Met Val Gln His Lys Asp Arg Phe Asn
                 85                  90                  95

Leu Leu Lys Glu Ile Leu Tyr Leu Lys Arg Thr Phe Ser Gly Lys His
            100                 105                 110

Phe Asp Gln Val Phe Val Ala Asn Ile Asn Asp Leu Gln Ile Gln Phe
        115                 120                 125

Leu Leu Ser Ala Ile Asp Phe Asn Leu Leu Asn Thr Phe Asp Asp Gly
130                 135                 140

Thr Ile Asn Ile Val Pro Asn Ser Leu Phe Tyr Gln Asp Asp Pro Ala
145                 150                 155                 160

Thr Leu Gln Arg Lys Leu Ile Asn Val Leu Leu Gly Asn Lys Tyr Ser
                165                 170                 175

Ile Gln Ser Leu Arg Ala Leu Ser His Thr His Tyr Thr Ile Tyr Lys
            180                 185                 190

Gly Phe Lys Asn Ile Ile Glu Arg Val Glu Pro Ile Glu Leu Val Ala
        195                 200                 205

Ala Asp Asn Ser Glu Lys Val Thr Ser Ala Val Ile Asn Val Leu Leu
210                 215                 220

Gly Gln Pro Val Phe Ala Glu Asp Glu Arg Asn Ile Ala Leu Ala Glu
225                 230                 235                 240

Arg Val Ile Lys Gln Phe Asn Ile His Tyr Tyr Leu Pro His Pro Arg
                245                 250                 255

Glu Lys Tyr Arg Leu Ala Gln Val Asn Tyr Ile Asp Thr Glu Leu Ile
            260                 265                 270

Phe Glu Asp Tyr Ile Leu Gln Gln Cys Gln Thr His Lys Tyr Cys Val
        275                 280                 285

Tyr Thr Tyr Phe Ser Ser Ala Ile Ile Asn Ile Met Asn Lys Ser Asp
290                 295                 300

Asn Ile Glu Val Val Ala Leu Lys Ile Asp Thr Glu Asn Pro Ala Tyr
305                 310                 315                 320

Asp Ala Cys Tyr Asp Leu Phe Asp Glu Leu Gly Val Asn Val Ile Asp
                325                 330                 335

Ile Arg Glu Leu Glu His His His His His His
            340                 345

<210> SEQ ID NO 6
<211> LENGTH: 707
<212> TYPE: PRT
<213> ORGANISM: Artificial Sequence
<220> FEATURE:
<223> OTHER INFORMATION: synthetic Pasteurella multocida strain P-1059
      (ATCC 15742) Pm0508 homolog sialidase-free monofunctional alpha-2,
      3-sialyltransferase N-terminal maltose binding protein (MBP)
      tagged and C-terminal His-6 tagged fusion protein MBP-PmST2-His-6
```

```
<400> SEQUENCE: 6

Met Lys Ile Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
 50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg Ile Ser Glu Phe Met Asn Leu Ile Ile Cys Cys Thr Pro
385                 390                 395                 400

Leu Gln Val Leu Ile Ala Glu Lys Ile Ile Ala Lys Phe Pro His Thr
                405                 410                 415
```

```
Pro Phe Tyr Gly Val Met Leu Ser Thr Val Ser Asn Lys Lys Phe Asp
            420                 425                 430

Phe Tyr Ala Lys Arg Leu Ala Gln Gln Cys Gln Gly Phe Ser Met
        435                 440                 445

Val Gln His Lys Asp Arg Phe Asn Leu Leu Lys Glu Ile Leu Tyr Leu
    450                 455                 460

Lys Arg Thr Phe Ser Gly Lys His Phe Asp Gln Val Phe Val Ala Asn
465                 470                 475                 480

Ile Asn Asp Leu Gln Ile Gln Phe Leu Leu Ser Ala Ile Asp Phe Asn
                485                 490                 495

Leu Leu Asn Thr Phe Asp Asp Gly Thr Ile Asn Ile Val Pro Asn Ser
            500                 505                 510

Leu Phe Tyr Gln Asp Asp Pro Ala Thr Leu Gln Arg Lys Leu Ile Asn
        515                 520                 525

Val Leu Leu Gly Asn Lys Tyr Ser Ile Gln Ser Leu Arg Ala Leu Ser
    530                 535                 540

His Thr His Tyr Thr Ile Tyr Lys Gly Phe Lys Asn Ile Ile Glu Arg
545                 550                 555                 560

Val Glu Pro Ile Glu Leu Val Ala Ala Asp Asn Ser Glu Lys Val Thr
                565                 570                 575

Ser Ala Val Ile Asn Val Leu Leu Gly Gln Pro Val Phe Ala Glu Asp
            580                 585                 590

Glu Arg Asn Ile Ala Leu Ala Glu Arg Val Ile Lys Gln Phe Asn Ile
        595                 600                 605

His Tyr Tyr Leu Pro His Pro Arg Glu Lys Tyr Arg Leu Ala Gln Val
    610                 615                 620

Asn Tyr Ile Asp Thr Glu Leu Ile Phe Glu Asp Tyr Ile Leu Gln Gln
625                 630                 635                 640

Cys Gln Thr His Lys Tyr Cys Val Tyr Thr Tyr Phe Ser Ser Ala Ile
                645                 650                 655

Ile Asn Ile Met Asn Lys Ser Asp Asn Ile Glu Val Val Ala Leu Lys
            660                 665                 670

Ile Asp Thr Glu Asn Pro Ala Tyr Asp Ala Cys Tyr Asp Leu Phe Asp
        675                 680                 685

Glu Leu Gly Val Asn Val Ile Asp Ile Arg Gly Lys Leu His His His
    690                 695                 700

His His His
705
```

<210> SEQ ID NO 7
<211> LENGTH: 2
<212> TYPE: PRT
<213> ORGANISM: Artificial Sequence
<220> FEATURE:
<223> OTHER INFORMATION: synthetic sialyltransferase motif A

<400> SEQUENCE: 7

Asp Glu
 1

<210> SEQ ID NO 8
<211> LENGTH: 3
<212> TYPE: PRT
<213> ORGANISM: Artificial Sequence
<220> FEATURE:
<223> OTHER INFORMATION: synthetic sialyltransferase motif B

```
<400> SEQUENCE: 8

Pro His Pro
  1

<210> SEQ ID NO 9
<211> LENGTH: 6
<212> TYPE: PRT
<213> ORGANISM: Artificial Sequence
<220> FEATURE:
<223> OTHER INFORMATION: synthetic C-terminal His-6 tag, fusion flag

<400> SEQUENCE: 9

His His His His His His
  1               5

<210> SEQ ID NO 10
<211> LENGTH: 36
<212> TYPE: DNA
<213> ORGANISM: Artificial Sequence
<220> FEATURE:
<223> OTHER INFORMATION: synthetic PCR amplification forward primer for
      cloning of PmST2-His-6 fusion protein

<400> SEQUENCE: 10
cgcggatcca tgaatttgat tatttgttgt acaccg                                36

<210> SEQ ID NO 11
<211> LENGTH: 33
<212> TYPE: DNA
<213> ORGANISM: Artificial Sequence
<220> FEATURE:
<223> OTHER INFORMATION: synthetic PCR amplification reverse primer for
      cloning of PmST2-His-6 fusion protein

<400> SEQUENCE: 11
ccgctcgagc tctcttatat caataacgtt aac                                  33

<210> SEQ ID NO 12
<211> LENGTH: 37
<212> TYPE: DNA
<213> ORGANISM: Artificial Sequence
<220> FEATURE:
<223> OTHER INFORMATION: synthetic PCR amplification forward primer for
      cloning of full-length MBP-PmST2-His-6 fusion protein

<400> SEQUENCE: 12
gaccgaattc atgaatttga ttatttgttg tacaccg                              37

<210> SEQ ID NO 13
<211> LENGTH: 50
<212> TYPE: DNA
<213> ORGANISM: Artificial Sequence
<220> FEATURE:
<223> OTHER INFORMATION: synthetic PCR amplification reverse primer for
      cloning of full-length MBP-PmST2-His-6 fusion protein

<400> SEQUENCE: 13
gatcaagctt ttagtggtgg tggtggtggt gctctcttat atcaataacg                50

<210> SEQ ID NO 14
<211> LENGTH: 304
<212> TYPE: PRT
<213> ORGANISM: Haemophilus influenzae
<220> FEATURE:
<223> OTHER INFORMATION: Haemophilus influenzae strain 86-028NP Pm0508
      homolog LsgB (HiLsgB), CMP-N-acetylneuraminate-beta-galactosamide-
      alpha-2,3-sialyltransferase (alpha 2,3-ST), lipooligosaccharide
``` sialyltransferase, locus NTHI2006

<400> SEQUENCE: 14

Met Asn Leu Ile Leu Cys Cys Thr Pro Leu Gln Val Leu Ile Ala Arg
1               5                   10                  15

Lys Ile Ile Glu Leu His Pro Asn Glu Gln Phe Phe Gly Val Met Phe
            20                  25                  30

Gly Arg Val Trp Asp Lys Lys Arg Thr Leu Tyr Ala Ser Lys Leu Ala
        35                  40                  45

Glu Val Cys Ser Asp Ser Met Asn Ile Asp Thr Gly Lys Asp Leu Lys
    50                  55                  60

Gly Phe Asp Phe Leu Lys Leu Met Arg Gln Leu Lys Asn Lys Ile Thr
65                  70                  75                  80

His Lys Gly Phe Asp Lys Val Phe Leu Ala Asn Leu Asn Ser Leu Trp
                85                  90                  95

Leu Gln Thr Tyr Leu Ser His Val Ser Phe Lys Glu Leu Tyr Thr Phe
            100                 105                 110

Asp Asp Gly Ser Asp Asn Ile Phe Pro His Pro Asn Leu Leu Arg Glu
        115                 120                 125

Pro Asp Thr Phe Lys Tyr Lys Leu Ile Lys Ala Phe Ile Gly Asp Lys
    130                 135                 140

Tyr Ser Val Asn Lys Leu Phe Lys Lys Ile Lys Lys His Tyr Thr Val
145                 150                 155                 160

Tyr Pro Asn Tyr Lys Asn Ile Val Ser Asn Ile Glu Pro Ile Ser Leu
                165                 170                 175

Trp Asp Asn Gln Ile Asp Cys Glu Ile Asp Gly Glu Val Ser Phe Phe
            180                 185                 190

Ile Gly Gln Pro Leu Leu Asn Thr Lys Glu Glu Asn Ile Ser Leu Ile
        195                 200                 205

Lys Lys Leu Lys Glu Gln Phe Ser Phe Asp Tyr Tyr Phe Pro His Pro
210                 215                 220

Ala Glu Asp Tyr Arg Val Asp Gly Val Asn Tyr Val Glu Ser Glu Leu
225                 230                 235                 240

Ile Phe Glu Asp Tyr Val Phe Lys Tyr Leu Ser Asn Lys Ile Ile Ile
                245                 250                 255

Ile Tyr Thr Phe Phe Ser Ser Val Ala Phe Asn Leu Leu Ser His Pro
            260                 265                 270

Asn Val Glu Ile Arg Phe Ile Arg Thr Ser Ile Pro Arg Trp Gln Phe
        275                 280                 285

Cys Tyr Asp Ser Phe Pro Asp Leu Gly Leu Lys Ile Tyr Lys Glu Ile
290                 295                 300

<210> SEQ ID NO 15
<211> LENGTH: 371
<212> TYPE: PRT
<213> ORGANISM: Neisseria meningitidis
<220> FEATURE:
<223> OTHER INFORMATION: Neisseria meningitidis strain MC58, NRCC 4728
      Pm0508 homolog Lst (NmLst) lipooligosaccharide
      alpha-2,3-sialyltransferase

<400> SEQUENCE: 15

Met Gly Leu Lys Lys Ala Cys Leu Thr Val Leu Cys Leu Ile Val Phe
1               5                   10                  15

Cys Phe Gly Ile Phe Tyr Thr Phe Asp Arg Val Asn Gln Gly Glu Arg
            20                  25                  30

-continued

```
Asn Ala Val Ser Leu Leu Lys Glu Lys Leu Phe Asn Glu Glu Gly Glu
            35                  40                  45
Pro Val Asn Leu Ile Phe Cys Tyr Thr Ile Leu Gln Met Lys Val Ala
 50                      55                  60
Glu Arg Ile Met Ala Gln His Pro Gly Glu Arg Phe Tyr Val Val Leu
 65                  70                      75                  80
Met Ser Glu Asn Arg Asn Glu Lys Tyr Asp Tyr Tyr Phe Asn Gln Ile
                 85                  90                  95
Lys Asp Lys Ala Glu Arg Ala Tyr Phe Phe His Leu Pro Tyr Gly Leu
            100                 105                 110
Asn Lys Ser Phe Asn Phe Ile Pro Thr Met Ala Glu Leu Lys Val Lys
            115                 120                 125
Ser Met Leu Leu Pro Lys Val Lys Arg Ile Tyr Leu Ala Ser Leu Glu
    130                 135                 140
Lys Val Ser Ile Ala Ala Phe Leu Ser Thr Tyr Pro Asp Ala Glu Ile
145                 150                 155                 160
Lys Thr Phe Asp Asp Gly Thr Gly Asn Leu Ile Gln Ser Ser Ser Tyr
                165                 170                 175
Leu Gly Asp Glu Phe Ser Val Asn Gly Thr Ile Lys Arg Asn Phe Ala
            180                 185                 190
Arg Met Met Ile Gly Asp Trp Ser Ile Ala Lys Thr Arg Asn Ala Ser
        195                 200                 205
Asp Glu His Tyr Thr Ile Phe Lys Gly Leu Lys Asn Ile Met Asp Asp
        210                 215                 220
Gly Arg Arg Lys Met Thr Tyr Leu Pro Leu Phe Asp Ala Ser Glu Leu
225                 230                 235                 240
Lys Thr Gly Asp Glu Thr Gly Gly Thr Val Arg Ile Leu Leu Gly Ser
                245                 250                 255
Pro Asp Lys Glu Met Lys Glu Ile Ser Glu Lys Ala Ala Lys Asn Phe
            260                 265                 270
Lys Ile Gln Tyr Val Ala Pro His Pro Arg Gln Thr Tyr Gly Leu Ser
            275                 280                 285
Gly Val Thr Thr Leu Asn Ser Pro Tyr Val Ile Glu Asp Tyr Ile Leu
    290                 295                 300
Arg Glu Ile Lys Lys Asn Pro His Thr Arg Tyr Glu Ile Tyr Thr Phe
305                 310                 315                 320
Phe Ser Gly Ala Ala Leu Thr Met Lys Asp Phe Pro Asn Val His Val
                325                 330                 335
Tyr Ala Leu Lys Pro Ala Ser Leu Pro Glu Asp Tyr Trp Leu Lys Pro
            340                 345                 350
Val Tyr Ala Leu Phe Thr Gln Ser Gly Ile Pro Ile Leu Thr Phe Asp
            355                 360                 365
Asp Lys Asn
370
```

PMST2 ENZYME FOR CHEMOENZYMATIC SYNTHESIS OF α-2-3-SIALYLGLYCOLIPIDS

CROSS-REFERENCES TO RELATED APPLICATIONS

This application claims priority to U.S. Provisional Application No. 61/585,376, filed Jan. 11, 2012, which is incorporated in its entirety herein for all purposes.

STATEMENT AS TO RIGHTS TO INVENTIONS MADE UNDER FEDERALLY SPONSORED RESEARCH AND DEVELOPMENT

This invention was made with Government support under Grant Nos. R01GM076360 and R01HD065122, awarded by the National Institutes of Health. The Government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -2108-1.TXT, created on Mar. 26, 2013, 28,672 bytes, machine format IBM-PC, MS-Windows operating system, is hereby incorporated by reference in its entirety for all purposes.

BACKGROUND OF THE INVENTION

Glycosyltransferase-catalyzed reactions have gained increasing attention and application for the synthesis of complex carbohydrates and glycoconjugates. Sialyltransferases, in particular, are the key enzymes that catalyze the transfer of a sialic acid residue from cytidine 5'-monophosphate-sialic acid (CMP-sialic acid) to an acceptor. Resulting sialic acid-containing products have been implicated in various biological and pathological processes, including cell-cell recognition, cell growth and differentiation, cancer metastasis, immunological regulation, as well as bacterial and viral infection. Besides being prevalent in mammals, sialyltransferases have been found in some pathogenic bacteria. They are mainly involved in the formation of sialic acid-containing capsular polysaccharides (CPS) and lipooligo(poly)saccharides (LOS/LPS), serving as virulence factors, preventing recognition by host's immune system, and modulating interactions with the environment. Sialyltransferases have been used for the synthesis of sialic acid-containing molecules with or without CMP-sialic acid biosynthetic enzymes.

Cloning of sialyltransferases from various sources, including mammalian tissues, bacteria, and viruses has been reported. Bacterial sialyltransferases have been cloned from several Gram-negative bacteria belonging to *Escherichia, Campylobacter, Neisseria, Photobacterium, Haemophilus,* and *Pasteurella* genera. The genera *Pasteurella* and *Haemophilus*, both belong to the *Haemophilus-Actinobacillus-Pasteurella* (HAP) group, generally produced negatively charged outer cell surface and contain multiple genes encoding functional sialyltransferases. Two functional α2,3-sialyltransferases encoded by 1st and Hd0053 have been identified from *Haemophilus ducreyi*. Lic3A, SiaA, LsgB, and Lic3B are four sialyltransferases involved in the complex process of lipopolysaccharide sialylation in *Haemophilus influenzae*.

Most mammalian glycosyltransferases—including sialyltransferases—suffer from no or low expression in *E. coli* systems and more restricted substrate specificity. In comparison, bacterial glycosyltransferases are generally easier to access using *E. coli* expression systems and have more promiscuous substrate flexibility. Although certain wild-type bacterial glycosyltransferases with promiscuities for both donor and acceptor substrates have been discovered, readily obtainable enzymes with a wider substrate tolerance are needed to further the application of glycosyltransferases. The present invention meets this and other needs, providing surprisingly useful sialyltransferases for synthesis of glycoconjugates.

BRIEF SUMMARY OF THE INVENTION

In a first aspect, the invention provides a method of preparing a glycolipid product. The method includes forming a reaction mixture containing an acceptor glycolipid, a donor substrate having a sugar moiety and a nucleotide, and a sialyltransferase selected from PmST2 (SEQ ID NO: 4) and certain variants thereof. In some embodiments, the donor substrate is formed via conversion of a suitable hexosamine derivative to a cytidine 5'-monophosphate (CMP)-sialic acid in a one-pot reaction mixture containing a sialic acid aldolase and a CMP-sialic acid synthetase.

In a second aspect, the invention provides an isolated or purified polynucleotide comprising a nucleotide sequence that is substantially identical to SEQ ID NO: 1 (PmST2) or certain variants thereof.

In a third aspect, the invention provides an isolated or purified polypeptide comprising an amino acid sequence selected from SEQ ID NO:4 (PmST2) and certain variants thereof.

BRIEF DESCRIPTION OF THE DRAWINGS

FIG. 1 shows the amino acid sequence alignment of PmST2 (a Pm0508protein homolog) (SEQ ID NO:4), HiLsgB from *Haemophilus influenzae* 86-028NP (GeneBank accession no. AAX88755) (SEQ ID NO:14), and NmLst from *Neisseria meningitidis* MC58(GeneBank accession no. AAC44541) (SEQ ID NO:15). Black boxes indicate identical or similar amino acid residues shared by all three sequences, while grey boxes indicate identical or similar amino acid residues shared by two of three sequences. In PmST2, the amino acid residue differing from the protein encoded by reported Pm0508 gene is marked with an asterisk (*) above the residue.

FIG. 4 shows the time course analysis of the α-2,3-sialyltransferase activity of PmST1(open circle, dashed line) and MBP-PmST2-His$_6$(filled diamond, solid line) using LacβPro2AA (A) or LacβPro-triazole-C14(B; 0.3% Triton X-100 was added) as the sialyltransferase acceptor.

DETAILED DESCRIPTION OF THE INVENTION

I. General

Figure 2:
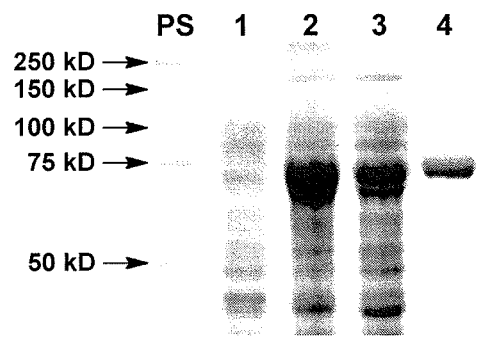
FIG. 2 shows the SDS-PAGE (12% Tris-Glycine gel) analysis of MBP-PmST2-His$_6$ expression and purification. Lanes: PS, protein standards (Precision Plus Protein Standards, Bio-Rad); 1, whole cell extraction, before IPTG induction; 2, whole cell extraction, after induction; 3, lysate after induction; and 4, Ni$^{2+}$-NTA column purified protein.
Figure 3:
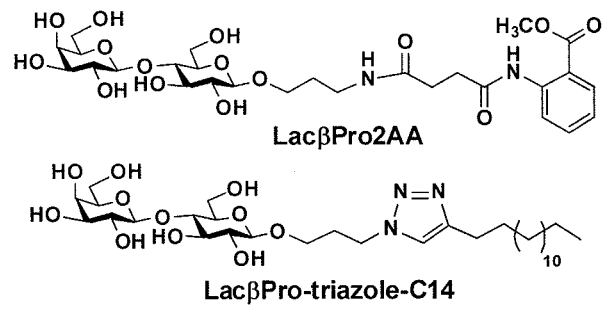
FIG. 3 shows the structures of LacβPro2AA and LacβPro-triazole-C14 used as acceptors for PmST2.
Figure 5:
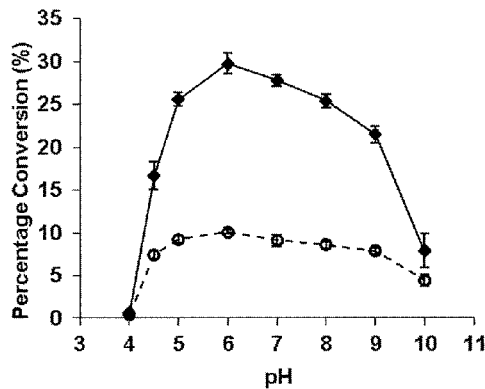
FIG. 5 shows the pH profile of MBP-PmST2-His$_6$-catalyzed α2-3-sialyltransferase reaction when LacβPro2AA (dashed line with open circles) or LacβPro-triazole-C14 (solid line with filled diamonds, 0.3% Triton X-100 was added) was used as the acceptor substrate. Buffers (200 mM) used: sodium acetate (pH 4.0-6.0), Tris-HCl (pH 7.0-9.0), and CHES (pH 10.0).

The present invention provides α2,3-sialyltransferases useful for the preparation of glycosylated molecules. In particular, the second sialyltransferase from *Pasteurella multocida* strain P-1059 (PmST2; encoded by gene Pm0508) is a sialidase-free monofunctional α2,3-sialyltransferase. Certain variants of soluble, active PmST2 can be obtained in high yield, making this enzyme desirable for large-scale synthesis of glycosylated products. The surprising monofunctionality of PmST2 is particularly advantageous, allowing for the preparation of a variety of sialic acid containing glycolipids.

II. Definitions

"Glycosyltransferase" refers to a polypeptide that catalyzes the formation of a glycoside or an oligosaccharide from a donor substrate and an acceptor or acceptor sugar. In general, a glycosyltransferase catalyzes the transfer of the monosaccharide moiety of the donor substrate to a hydroxyl group of the acceptor. The covalent linkage between the monosaccharide and the acceptor sugar can be a 1-4 linkage, a 1-3 linkage, a 1-6-linkage, a 1-2 linkage, a 2-3-linkage, a 2-4-linkage, a 2-6-linkage, a 2-8-linkage, or a 2-9-linkage. The linkage may be in the α- or β-configuration with respect to the anomeric carbon of the monosaccharide. Other types of linkages may be formed by the glycosyltransferases in the methods of the invention. Glycosyltransferases include, but are not limited to, sialyltransferases, heparosan synthases (HSs), glucosaminyltransferases, N-acetylglucosaminyltransferases, glucosyltransferases, glucuronyltransferases, N-acetylgalactosaminyltransferases, galactosyltransferases, galacturonyltransferases, fucosyltransferases, mannosyltransferases, xylosyltransferases. Sialyltransferases are enzymes that catalyze the transfer of sialic acid, or analogs thereof, to a monosaccharide, an oligosaccharide, or a glycoconjugate. In some embodiments, the glycosyltransferases useful in the present invention include those in Glycosyltransferase family 52 (GT52 using Carbohydrate-Active enZYme database (CAZy) nomenclature), and includes beta-galactoside alpha-2,3-sialyltransferases that catalyze the following conversion: CMP-sialic acid+β-D-galactosyl-R=CMP+α-sialic acid-(2→3)-β-D-galactosyl-R, where the acceptor is GalβOR, where R is H, a monosaccharide, an oligosaccharide, a polysaccharide, a glycopeptide, a glycoprotein, a glycolipid, or a hydroxyl-containing compound. GT80 family sialyltransferases also include galactoside or N-acetylgalactosaminide alpha-2,6-sialyltransferases that catalyze the following conversion: CMP-sialic acid+galactosyl/GalNAcOR→CMP+α-sialic acid-(2→6)-D-galactosyl/GalNAcOR, where the acceptor is GalOR or GalNAcOR, where R is H, serine or threonine on a peptide or protein, a monosaccharide, an oligosaccharide, a polysaccharide, a glycopeptide, a glycoprotein, a glycolipid, or a hydroxyl-containing compound.

"Sialidase" refers to an enzyme that catalyzes the hydrolysis of glycosidic linkages of terminal sialic acids on glycosylated molecules.

"Donor substrate hydrolysis" refers to hydrolysis of O-glycosidic bond of the sugar and the phosphate in the nucleotide-sugar donor substrate.

"Amino acid" refers to any monomeric unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (H is or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., *Biochemistry*, 5$^{th}$ ed., Freeman and Company (2002), which is incorporated by reference. Additional amino acids, such as selenocysteine and pyrrolysine, can also be genetically coded for (Stadtman (1996) "Selenocysteine," *Annu Rev Biochem.* 65:83-100 and Ibba et al. (2002) "Genetic code: introducing pyrrolysine," *Curr Biol.* 12(13):R464-R466, which are both incorporated by reference). The term "amino acid" also includes unnatural amino acids, modified amino acids (e.g., having modified side chains and/or backbones), and amino acid analogs.

"Polypeptide," "peptide," and "protein" are used interchangeably herein to refer to a polymer of amino acid residues. All three teams apply to amino acid polymers in which one or more amino acid residue is an artificial chemical mimetic of a corresponding naturally occurring amino acid, as well as to naturally occurring amino acid polymers and non-natural amino acid polymers. As used herein, the terms encompass amino acid chains of any length, including full-length proteins, wherein the amino acid residues are linked by covalent peptide bonds.

"Mutant," in the context of glycosyltransferases of the present invention, means a polypeptide, typically recombinant, that comprises one or more amino acid substitutions relative to a corresponding, naturally-occurring or unmodified glycosyltransferase, such as an alpha2-3 sialyltransferase.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

"Percent sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

"Identical" or "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% identity over a specified region), when compared and aligned for maximum correspondence over a comparison window, or designated region as measured using one of the following sequence comparison algorithms or by manual alignment and visual inspection. These definitions also refer to the complement of a test sequence. Optionally, the identity exists over a region that is at least about 50 nucleotides in length, or more typically over a region that is 100 to 500 or 1000 or more nucleotides in length.

"Similarity" or "percent similarity," in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other. Optionally, this similarly exists over a region that is at least about 50 amino acids in length, or more typically over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Algorithms suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

"Recombinant," as used herein, refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated, mutant glycosyltransferase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above.

"Vector" refers to a piece of DNA, typically double-stranded, which may have inserted into it a piece of foreign DNA. The vector may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

"Nucleotide," in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

"Nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (*Science* 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

"Forming a reaction mixture" refers to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

"Donor substrate" refers to a compound having a nucleotide and a sugar moiety that is added to an acceptor, where the sugar moiety and nucleotide are covalently bound together. In general, the sugar moiety is characterized by monosaccharide core having a linear formula of $H(CHOH)_n(CO)(CHOH)_mH$, wherein the sum of n and m is at least 2. In certain embodiments, the sum of n and m is 5. In certain embodiments, n is 5 and m is 0. Any H or OH group in the monosaccharide core can be replaced by an amine group $NHR'$, wherein $R'$ is selected from H, alkyl, and acyl. One of skill in the art will appreciate that the monosaccharide core can be in the linear form or in the cyclic, hemiacetal form. The hemiacetal can be a pyranose (i.e., a six-membered ring) or a furanose (i.e., a five-membered ring). In general, the hydroxyl group at the anomeric carbon of the hemiacetal is the point of connection between the sugar moiety and the nucleotide in the donor substrate. The monosaccharide core of the sugar moiety can be substituted with various functional groups as described herein. In certain embodiments, the monosaccharide core of the sugar moiety is substituted with pyruvate. In certain embodiments, the sugar moiety is sialic acid or analog thereof. The nucleotide in the donor substrate can be any suitable nucleotide, such as cytidine monophosphate (CMP).

"Acceptor glycolipid" refers to a lipid containing a sugar that accepts the sugar moiety from the donor substrate. The sugar of the glycolipid can be a monosaccharide or an oligosaccharide as defined herein. In certain embodiments, the acceptor glycolipid contains a galactoside moiety, wherein the hydroxyl group at the anomeric carbon of the galactopyranose ring is the point of connection to the remainder of the glycolipid. In some embodiments, the galactoside moiety is a β1-4 linked galactoside moiety or a β1-3 linked galactoside moiety. In certain embodiments, the acceptor glycolipid contains a lactoside moiety having a 4-O-β-D-galactopyranosyl-D-glucopyranose disaccharide unit. The hydroxyl group at the anomic carbon of the glucopyranose ring is the point of connection between the lactoside moiety and the remainder of the glycolipid. In some embodiments, the acceptor glycolipid comprises an N-acetyl lactoside moiety, a Galβ1-3GlcNAc moiety, or a Galβ1-3GalNAc moiety.

"Oligosaccharide" refers to a compound containing at least two sugars covalently linked together. Oligosaccharides include disaccharides, trisaccharides, tetrasachharides, pentasaccharides, hexasaccharides, heptasaccharides, octasaccharides, and the like. Covalent linkages for linking sugars generally consist of glycosidic linkages (i.e., C—O—C bonds) formed from the hydroxyl groups of adjacent sugars. Linkages can occur between the 1-carbon (the anomeric carbon) and the 4-carbon of adjacent sugars (i.e., a 1-4 linkage), the 1-carbon (the anomeric carbon) and the 3-carbon of adjacent sugars (i.e., a 1-3 linkage), the 1-carbon (the anomeric carbon) and the 6-carbon of adjacent sugars (i.e., a 1-6 linkage), or the 1-carbon (the anomeric carbon) and the 2-carbon of adjacent sugars (i.e., a 1-2 linkage). A sugar can be linked within an oligosaccharide such that the anomeric carbon is in the α- or β-configuration. The oligosaccharides prepared according to the methods of the invention can also include linkages between carbon atoms other than the 1-, 2-, 3-, 4-, and 6-carbons.

"Glycolipid" refers to a lipid containing a sugar moiety or an oligosaccharide moiety. Examples of glycolipids include, but are not limited to, glycoglycerolipids, glycosphingolipids, glycosyl polyisoprenol pyrophosphates, and glycosylphosphatidylinositols. A "glycolipid product" is a glycolipid formed by an enzymatic reaction, such as a PmST-catalyzed reaction.

"CMP-sialic acid synthetase" refers to a polypeptide that catalyzes the synthesis of cytidine monophosphate sialic acid (CMP-sialic acid) from cytidine triphosphate (CTP) and sialic acid.

"Sialic acid aldolase" refers to an aldolase that catalyzes a reversible reaction that converts a suitable hexosamine, hexose, pentose, or derivative (such as N-acetyl mannosamine) to sialic acid via reaction with pyruvate.

III. Sialyltransferases

Sialyltransferases are one class of glycosyltransferases, enzymes that catalyze the transfer of a sugar from a nucleotide-sugar (donor substrate) to an acceptor (e.g., a natural product, a monosaccharide, an oligosaccharide, a glycolipid, a glycoprotein, or a hydroxyl-containing compounds). Specifically, sialyltransferases catalyze the transfer of sialic acid, or analogs thereof, from a sialic acid-nucleotide donor substrate to the terminal sugar of an acceptor substrate. Representative sialyltransferases include, but are not limited to, sialyltransferases in family EC 2.4.99, such as beta-galactosaminide alpha-2,6-sialyltransferase (EC 2.4.99.1), alpha-N-acetylgalactosaminide alpha-2,6-sialyltransferase (EC 2.4.99.3), beta-galactoside alpha-2,3-sialyltransferase (EC 2.4.99.4), N-acetyllactosaminide alpha-2,3-sialyltransferase (EC 2.4.99.6), alpha-sialyl alpha-2,8-sialyltransferase (EC 2.4.99.8), and lactosylceramide alpha-2,3-sialyltransferase (EC 2.4.99.9). The sialyltransferases of the present invention also include those of the CAZy GT52 family, or EC 2.4.99.4 and EC 2.4.99.1, made up of alpha2-3 and alpha2-6 sialyltransferases, as well as sialyltransferases in the GT4, GT29, GT30, GT38, GT42, GT73, and GT80 families. Representative GT52 sialyltransferases include, but are not limited to, PmST2, *Salmonella enterica* WaaH, *Neisseria meningitidis* Lst, *Neisseria gonorrhoeae* Lst, and NST. (See Glycobiology 2011, 21(6), 716; J. Mol. Biol. 2003, 328, 307; Annu. Rev. Biochem. 2008, 77, 521; Appl. Microbiol. Biotechnol. 2012, 94, 887 for review of sialyltransferases.) PmST2 is a preferred sialyltransferase in some embodiments of the invention.

In general, the sialyltransferases of the present invention are α-2,3-sialyltransferases. The α2,3-sialyltransferases of the present invention can include sialyltransferases of *Pasteurella multocida*. The sialyltransferases include those having decreased α2,3-sialidase activity compared to a control glycosyltransferase. α2,3-sialidase activity, in particular, refers to the cleavage of the glycosidic bond between the sialic acid from the donor substrate and the sugar of the acceptor molecule, which results in free sialic acid and the acceptor. For certain sialyltransferases of the invention, this activity is essentially absent.

The sialyltransferases of the present invention can include a polypeptide having any suitable percent identity to a reference sequence (e.g., SEQ ID NO: 4). For example, the glycosyltransferases of the present invention can include a polypeptide having a percent sequence identity to the control glycosyltransferase sequence of at least 20, 30, 40, 50, 55, 60, 65, 70, 75, 80, 85, 90, 91, 92, 93, 94, 95, 96, 97, 98 or at least 99%. In some embodiments, percent sequence identity can be at least 80%. In some embodiments, percent sequence identity can be at least 90%. In some embodiments, percent sequence identity can be at least 95%.

In some embodiments, the invention provides an isolated or purified polypeptide including an amino acid sequence selected from SEQ ID NO: 4 (PmST2); SEQ ID NO: 5 (PmST2-His$_6$); and SEQ ID NO: 6 (MBP-PmST2-His$_6$). In some embodiments, the polypeptide comprises an amino acid sequence selected from SEQ ID NO: 7 (sialyltransferase motif A), and SEQ ID NO: 8 (sialyltransferase motif B).

The precise length of the sialyltransferases can vary, and certain variants can be advantageous for expression and purification of the enzymes with high yields. For example, removal of certain peptide subunits from the overall polypeptide sequence of a sialyltransferase can improve solubility of the enzyme and increase expression levels. Alternatively, addition of certain peptide or protein subunits to a sialyltransferase polypeptide sequence can modulate expression, solubility, activity, or other properties. The sialyltransferases of the present invention can include point mutations at any position of the PmST2 wild type sequence or a PmST2 variant (e.g., a fusion protein or a truncated form). The mutants can include any suitable amino acid other than the native amino acid. For example, the amino acid can be V, I, L, M, F, W, P, S, T, A, G, C, Y, N, Q, D, E, K, R, or H. Amino acid and nucleic acid sequence alignment programs are readily available (see, e.g., those referred to supra) and, given the particular motifs identified herein, serve to assist in the identification of the exact amino acids (and corresponding codons) for modification in accordance with the present invention.

The sialyltransferases of the present invention can be constructed by mutating the DNA sequences that encode the corresponding unmodified sialyltransferase (e.g., a wild-type sialyltransferase or a corresponding variant), such as by using techniques commonly referred to as site-directed mutagenesis. Nucleic acid molecules encoding the unmodified form of the sialyltransferase can be mutated by a variety of techniques well-known to one of ordinary skill in the art. (See, e.g., *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, NY, 1990).

By way of non-limiting example, the two primer system, utilized in the Transformer Site-Directed Mutagenesis kit from Clontech, may be employed for introducing site-directed mutants into a polynucleotide encoding an unmodified form of the sialyltransferase. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids result in high mutation efficiency and allow minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Mutagenesis can also be conducted using a QuikChange multisite-directed mutagenesis kit (Stratagene) and the like. Transformants can be screened by sequencing the plasmid DNA through the mutagenized region to identify and sort mutant clones. Each mutant DNA can then be restricted and analyzed by electrophoresis, such as for example, on a Mutation Detection Enhancement gel (Mallinckrodt Baker, Inc., Phillipsburg, N.J.) to confirm that no other alterations in the sequence have occurred (by band shift comparison to the unmutagenized control). Alternatively, the entire DNA region can be sequenced to confirm that no additional mutational events have occurred outside of the targeted region.

Verified mutant duplexes in pET (or other) overexpression vectors can be employed to transform E. coli such as, e.g., strain E. coli BL21 (DE3) or strain E. coli BL21 (DE3) pLysS, for high level production of the mutant protein, and purification by standard protocols. The method of FAB-MS mapping, for example, can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutated protein). The set of cleavage fragments is fractionated by, for example, HPLC (reversed phase or ion exchange, again depending on the specific region to be modified) to provide several peptides in each fraction, and the molecular weights of the peptides are determined by standard methods, such as FAB-MS. The determined mass of each fragment are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS data agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

Recombinant Nucleic Acids

Sialyltransferase variants can be generated in various ways. In the case of amino acids located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: DNA encoding the unmodified sialyltransferase is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on. Alternatively, the multi-site mutagenesis method of Seyfang & Jin (Anal. Biochem. 324:285-291. 2004) may be utilized.

Accordingly, also provided are recombinant nucleic acids, optionally isolated, encoding any of the sialyltransferases of the present invention. In some embodiments, the invention provides an isolated or purified polynucleotide including a nucleotide sequence that is substantially identical to a sequence selected from SEQ ID NO:1 (PmST2), SEQ ID NO:2 (PmST2-His$_6$), and SEQ ID NO:3 (MBP-PmST2-His$_6$), or complements thereof. In some embodiments, the polynucleotide includes a nucleotide sequence that is substantially identical to a sequence selected from SEQ ID NO:1 (PmST2), SEQ ID NO:2 (PmST2-His$_6$), and SEQ ID NO:3 (MBP-PmST2-His$_6$), or complements thereof. In some embodiments, the polynucleotide comprises a polynucleotide sequence encoding SEQ ID NO: 7 (sialyltransferase motif A) or SEQ ID NO: 8 (sialyltransferase motif B), or the complement of a sequence that encodes SEQ ID NO: 7 or 8. In general, the polynucleotide has at least 50% sequence identity to a sequence selected from SEQ ID NOS: 1, 2, and 3, and complements thereof. The sequence identity can be, for example, 50%, 55%, 60%, 65%, 70%, 75%, 80%, 85%, 90%, 91%, 92%, 93%, 94%, 95%, 96%, 97%, 98%, 99%, or 100%. In some embodiments, a given polynucleotide can be optimized for expression in yeast. In some embodiments, the polynucleotide contains a sequence selected from SEQ ID NOS: 1, 2, and 3, and complements thereof.

Using a nucleic acid of the present invention, encoding a sialyltransferase of the invention, a variety of vectors can be made. Any vector containing replicon and control sequences that are derived from a species compatible with the host cell can be used in the practice of the invention. Generally, expression vectors include transcriptional and translational regulatory nucleic acid regions operably linked to the nucleic acid encoding the mutant sialyltransferase. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. In addition, the vector may contain a Positive Retroregulatory Element (PRE) to enhance the half-life of the transcribed mRNA (see Gelfand et al. U.S. Pat. No. 4,666,848). The transcriptional and translational regulatory nucleic acid regions will generally be appropriate to the host cell used to express the sialyltransferase. Numerous types of appropriate expression vectors, and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. In typical embodiments, the regulatory sequences include a promoter and transcriptional start and stop sequences. Vectors also typically include a polylinker region containing several restriction sites for insertion of foreign DNA. In certain embodiments, "fusion flags" are used to facilitate purification and, if desired, subsequent removal of tag/flag sequence, e.g., "His-Tag". However, these are generally unnecessary when purifying an thermoactive and/or thermostable protein from a mesophilic host (e.g., E. coli) where a "heat-step" may be employed. The construction of suitable vectors containing DNA encoding replication sequences, regulatory sequences, phenotypic selection genes, and the mutant sialyltransferase of interest are prepared using standard recombinant DNA procedures. Isolated plasmids, viral vectors, and DNA fragments are cleaved, tailored, and ligated together in a specific order to generate the desired vectors, as is well-known in the art (see, e.g., Sambrook et al., *Molecular Cloning: A Laboratory Manual* (Cold Spring Harbor Laboratory Press, New York, N.Y., 2nd ed. 1989)). In some embodiments, the present invention provides a recombinant nucleic acid encoding an isolated sialyltransferase of the present invention.

Host Cells

In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In one aspect of the present invention, a nucleic acid encoding a sialyltransferase of the invention is introduced into a cell, either alone or in combination with a vector. By "introduced into" or grammatical equivalents herein is meant that the nucleic acids enter the cells in a manner suitable for subsequent integration, amplification, and/or expression of the nucleic acid. The method of introduction is largely dictated by the targeted cell type. Exemplary methods include CaPO$_4$ precipitation, liposome fusion, LIPOFECTIN®, electroporation, viral infection, and the like.

In some embodiments, prokaryotes are used as host cells for the initial cloning steps of the present invention. Other host cells include, but are not limited to, eukaryotic (e.g., mammalian, plant and insect cells), or prokaryotic (bacterial) cells. Exemplary host cells include, but are not limited to, *Escherichia coli, Saccharomyces cerevisiae, Pichia pastoris*, Sf9 insect cells, and CHO cells. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325), *E. coli* K12 strain DG116 (ATCC No. 53,606), *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various *Pseudomonas* species can all be used as hosts. Prokaryotic host cells or other host cells with rigid cell walls are typically transformed using the calcium chloride method as described in section 1.82 of Sambrook et al., supra. Alternatively, electroporation can be used for transformation of these cells. Prokaryote transformation techniques are set forth in, for example Dower, in *Genetic Engineering, Principles and Methods* 12:275-296 (Plenum Publishing Corp., 1990); Hanahan et al., *Meth. Enzymol.*, 204:63, 1991. Plasmids typically used for transformation of *E. coli* include pBR322, pUCI8, pUCI9, pUCI18, pUCI19, and Bluescript M13, all of which are described in sections 1.12-1.20 of Sambrook et al., supra. However, many other suitable vectors are available as well.

In some embodiments, the sialyltransferases of the present invention are produced by culturing a host cell transformed with an expression vector containing a nucleic acid encoding the sialyltransferase, under the appropriate conditions to induce or cause expression of the sialyltransferase. Methods of culturing transformed host cells under conditions suitable for protein expression are well-known in the art (see, e.g., Sambrook et al., supra). Suitable host cells for production of the sialyltransferases from lambda pL promoter-containing plasmid vectors include *E. coli* strain DG116 (ATCC No. 53606) (see U.S. Pat. No. 5,079,352 and Lawyer, F. C. et al., *PCR Methods and Applications* 2:275-87, 1993, which are both incorporated herein by reference). Following expression, the sialyltransferase can be harvested and isolated. Methods for purifying thermostable glycosyltransferases are described in, for example, Lawyer et al., supra. In some embodiments, the present invention provides a cell including a recombinant nucleic acid of the present invention. In some embodiments, the cell can be prokaryotes, eukaryotes, mammalian, plant, bacteria or insect cells.

IV. Methods of Making Oligosaccharides

The sialyltransferases of the present invention can be used to prepare oligosaccharides, specifically to add N-acetylneuraminic acid (Neu5Ac), other sialic acids, and analogs thereof, to a glycolipid. For example, PmST2 can catalyze the addition of CMP-Neu5Ac to a lactosyl glycolipid by transferring the Neu5Ac to the lactoside moiety of the lactosyl glycolipid.

Accordingly, some embodiments of the present invention provide a method of preparing a glycolipid product. The method includes forming a reaction mixture containing an acceptor glycolipid, a donor substrate having a sugar moiety and a nucleotide, and a glycosyltransferase of the present invention. The glycosyltransferase includes a polypeptide having a sequence that is selected from SEQ ID NO:4 (PmST2), SEQ ID NO:5 (PmST2-His$_6$), and SEQ Ill NO:6 (MBP-PmST2-His$_6$). The reaction mixture is formed under conditions sufficient to transfer the sugar moiety from the donor substrate to the acceptor glycolipid, thereby forming the glycolipid product.

Any suitable acceptor glycolipid can be used in the methods of the invention. Suitable acceptor glycolipids include, but are not limited to, glycoglycerolipids (such as monogalactosyldiacylglycerols, digalactosylmonoacylglycerols, and sulfoquinovosyl diacylglycerols), glycosphingolipids (such as lacto-, neolacto-, ganglio-, globo-, and iso-globo-series glycosphingolipids), and glycosylphosphatidylinositols (e.g., 1-phosphatidyl-L-myo-inositol 2,6-di-O-α-D-mannopyranoside.). In some embodiments, the acceptor glycolipid comprises a galactoside moiety. In some embodiments, the galactoside moiety is selected from the group consisting of a β1-4 linked galactoside moiety and a β1-3 linked galactoside moiety. In some embodiments, the acceptor glycolipid comprises a lactoside moiety or an N-acetyl lactoside moiety. In some embodiments, the acceptor glycolipid comprises a Galβ1-3GlcNAc moiety or a Galβ1-3GalNAc moiety.

The donor substrate of the present invention includes a nucleotide and sugar. Suitable nucleotides include, but are not limited to, adenine, guanine, cytosine, uracil and thymine nucleotides with one, two or three phosphate groups. In some embodiments, the nucleotide can be cytidine monophosphate (CMP). The sugar can be any suitable sugar. For example, the sugar can be N-acetylneuraminic acid (Neu5Ac) or other sialic acids and analogs thereof. Sialic acid is a general term for N- and O-substituted derivatives of neuraminic acid, and includes, but is not limited to, N-acetyl (Neu5Ac) or N-glycolyl (Neu5Gc) derivatives, as well as O-acetyl, O-lactyl, O-methyl, O-sulfate and O-phosphate derivatives. In some embodiments, the sialic acid can be a compound of the formula:

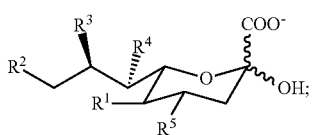

wherein $R^1$ is selected from H, OH, $N_3$, NHC(O)Me, NHC(O)CH$_2$OH, NHC(O)CH$_2$N$_3$, NHC(O)OCH$_2$C≡CH, NHC(O)CH$_2$F, NHC(O)CH$_2$NHCbz, NHC(O)CH$_2$OC(O)Me, and NHC(O)CH$_2$OBn; and $R^2$, $R^3$, $R^4$, and $R^5$ are independently selected from H, OH, $N_3$, OMe, F, $OSO_3^-$, $OPO_3H^-$, and OC(O)Me. In some embodiments, the donor substrate is a cytidine 5'-monophosphate (CMP)-sialic acid. In some embodiments, the CMP-sialic acid is cytidine 5'-monophosphate N-acetylneuraminic acid (CMP-Neu5Ac) or a CMP-Neu5Ac analog. Other donor substrates are useful in the methods of the present invention. In other embodiments, the sialic acid can be a compound of the formula:

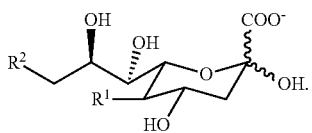

In some embodiments, the sialic acid donor can be a compound of the formula:

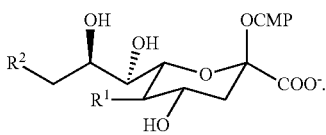

The methods of the invention include providing reaction mixtures that contain the sialyltransferases described herein. The sialyltransferases can be, for example, purified prior to addition to the reaction mixture or secreted by a cell present in the reaction mixture. Alternatively, a sialyltransferase can catalyze the reaction within a cell expressing the sialyltransferase.

Reaction mixtures can contain additional reagents for use in glycosylation techniques. For example, in certain embodiments, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, tetrahydrofuran, acetone, and acetic acid), salts (e.g., NaCl, KCl, CaCl$_2$, and salts of Mn$^{2+}$ and Mg$^{2+}$), chelators (e.g., ethylene glycol-bis(2-aminoethylether)-N,N,N',N'-tetraacetic acid (EGTA), 2-({2-[Bis(carboxymethyl)amino]ethyl}(carboxymethyl)amino)acetic acid (EDTA), and 1,2-bis(o-aminophenoxy)ethane-N,N,N',N'-tetraacetic acid (BAPTA)), reducing agents (e.g., dithiothreitol (DTT), β-mercaptoethanol (BME), and tris(2-carboxyethyl)phosphine (TCEP)), and labels (e.g., fluorophores, radiolabels, and spin labels). Buffers, cosolvents, salts, chelators, reducing agents, and labels can be used at any suitable concentration, which can be readily determined by one of skill in the art.

In general, buffers, cosolvents, salts, chelators, reducing agents, and labels are included in reaction mixtures at concentrations ranging from about 1 µM to about 1 M. For example, a buffer, a cosolvent, a salt, a chelator, a reducing agent, or a label can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M.

Reactions are conducted under conditions sufficient to transfer the sugar moiety from a donor substrate to an glycolipid. The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 4.5 to about 10. The reactions can be conducted, for example, at a pH of from about 5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Other reaction conditions may be employed in the methods of the invention, depending on the identity of a particular sialyltransferase, donor substrate, or acceptor molecule.

The donor substrate can be prepared prior to preparation of the oligosaccharide, or prepared in situ immediately prior to preparation of the oligosaccharide. In some embodiments, the method of the present invention also includes forming a reaction mixture including a CMP-sialic acid synthetase, cytidine triphosphate, and N-acetylneuraminic acid (Neu5Ac) or a Neu5Ac analog, under conditions suitable to form CMP-Neu5Ac or a CMP-Neu5Ac analog. Any suitable CMP-sialic acid synthetase (i.e., N-acylneuraminate cytidylyltransferase, EC 2.7.7.43) can be used in the methods of the invention. For example, CMP-sialic acid synthetases from E. coli, C. thermocellum, S. agalactiae, P. multocida, H ducreyi, or N. meningitidis can be used. In some embodiments, the step of forming the donor substrate and the step of forming the oligosaccharide are performed in one pot.

In some embodiments, the sugar moiety of the donor substrate is prepared separately prior to use in the methods of the present invention. Alternatively, the sugar moiety can be prepared in situ immediately prior to use in the methods of the present invention. In some embodiments, the method also includes forming a reaction mixture including a sialic acid aldolase, pyruvic acid or derivatives thereof, and N-acetylmannosamine or derivatives thereof, under conditions suitable to form Neu5Ac or a Neu5Ac analog. Any suitable sialic acid aldolase (i.e., N-acetylneuraminate pyruvate lyase, EC 4.1.3.3) can be used in the methods of the invention. For example, sialic acid aldolases from E. coli, L. plantarum, P. multocida, or N. meningitidis can be used. In some embodiments, the step of forming the sugar moiety, the step of forming the donor substrate, and the step of forming the oligosaccharide are performed in one pot.

The products prepared by the method of the present invention can include a variety of glycolipid products. In some embodiments, the glycolipid product is an 2,3-linked sialylglycolipid. In some embodiments, the α2,3-linked sialylglycolipid is Neu5Acα2-3lactosyl sphingosine (lyso-GM3) or a derivative thereof.

V. EXAMPLES

General Materials and Methods

Chemicals and Reagents. T4 DNA ligase, 1 kb DNA ladder, and BamHI restriction enzyme were obtained from Promega (Madison, Wis.). Herculase enhanced DNA polymerase was from Stratagene (La Jolla, Calif.). DNeasy Tissue kit, QIAprep spin miniprep kit, and QIAEX II gel extraction kit were bought from Qiagen (Valencia, Calif.). Nickel-nitrilotriacetic acid ($Ni^{2+}$-NTA) agarose was obtained from Fisher Scientific (Tustin, Calif.). Precision Plus Protein Standards and BioGel P-2 fine resin were from Bio-Rad (Hercules, Calif.). Bicinchoninic acid (BCA) protein assay kit was from Pierce Biotechnology, Inc. (Rockford, Ill.). Gel filtration LMW calibration kit and Superdex 75 10/300 GL column were from Amersham Biosciences (Piscataway, N.J.). Cytidine 5'-triphosphate (CTP), N-acetylmannosamine (ManNAc), and pyruvate were purchased from Sigma (St. Louis, Mo.). The sialyltransferase sugar nucleotide donor cytidine 5'-monophosphate N-acetylneuraminic acid (CMP-Neu5Ac) was synthesized enzymatically from ManNAc, pyruvate (5 equiv.), and CTP using a one-pot two-enzyme system containing a recombinant sialic acid aldolase cloned from E. coli K12 and a recombinant N. meningitidis CMP-sialic acid synthetase (NmCSS) as described previously. Lactosyl sphingosine and lactosyl ceramide were purchased from Avanti Polar Lipids Inc. (Alabaster, Ala.).

Bacterial strains and plasmids. Electrocompetent E. coli DH5α cells and chemically competent E. coli BL21(DE3) cells were from Invitrogen (Carlsbad, Calif.). Genomic DNA was prepared from Pasteurella multocida P-1059 from American Type Culture Collection (ATCC, Manassas, Va.) (ATCC#15742). Restriction enzymes XhoI, BamHI, EcoRI, and HindIII, and the expression vector pMal-c4X were purchased from New England Biolabs (Ipswich/Beverly, Mass.). Expression vector pET22b(+) was purchased from Novagen (EMD Biosciences, Inc. Madison, Wis.).

Analytical Methods. DNA sequencing was performed by Davis Sequencing Facility in the University of California-Davis. High resolution electrospray ionization (ESI) mass spectra were obtained at the Mass Spectrometry Facility in the University of California, Davis. All NMR experiments were carried out at 26° C. in $D_2O$ or $CD_3OD$ on Varian VNMRS 600 MHz or Bruker 800 MHz spectrometry. LacβPro2AA, LacβPro-triazole-C14, Galβ1-4GlcNAcβPro-triazole-C14 (LacNAcβPro-triazole-C14), Galβ1-3GlcNAcβPro-triazole-C14, Galβ1-3GlcNAcαPro-triazole-C14, Galβ1-3GalNAcαPro-triazole-C14, and GalβPro-triazole-C14 were synthesized as described in the Supporting Information.

Example 1

Cloning, Expression, and Purification of Pm0508 Homolog from Pm Strain P-1059 (ATCC 15742)

Methods

Cloning. The Pm0508 gene locus (GenBank accession no. AAK02592) was amplified by polymer chain reaction (PCR) from Pasteurella multocida P-1059(ATCC 15742) genomic DNA. Full-length Pm0508 gene was cloned as either a C-$His_6$ (SEQ ID NO:9) tagged or an N-terminal Maltose Binding Protein (MBP)-tagged and C-terminal $His_6$ (SEQ ID NO:9) tagged fusion protein. A forward primer 5'-CGC GGATCCATGAATTTGATTATTTGTTGTACACCG-3' (SEQ ID NO:10) (BamHI restriction site is underlined) and a reverse primer 5'-CCG CTCGAGCTCTCTTATATCAATAACGTTAAC-3' (SEQ ID NO:11) (XhoI restriction site is underlined) were used to clone the C-$His_6$ (SEQ ID NO:9) tagged fusion protein PmST2-$His_6$ in pET22b(+) vector. A forward primer 5'-GACC GAATTCATGAATTTGATTATTTGTTGTACACCG-3' (SEQ ID NO:12) (EcoRI restriction site is underlined) and a reverse primer 5'-GATC AAGCTTTTAGTGGTGGTGGTGGTGGTGCTCTCTTAT ATCAATAACG-3' (SEQ ID NO:13) (HindIII restriction site is underline and the codons for the C-$His_6$ (SEQ ID NO:9) tag are in italics) were used to clone of the full-length MBP-PmST2-$His_6$ fusion protein in pMa1-c4X vector. The C-$His_6$ (SEQ ID NO:9) tag was introduced to simplify purification using $Ni^{2+}$-NTA resin. The resulting PCR product was purified, digested, and inserted into the corresponding pre-digested vector DNAs by ligation. The ligation product was transformed into electrocompetent E. coli DH5α cells. Positive plasmids were selected and subsequently transformed into BL21(DE3) chemically competent cells.

Expression and Purification of MBP-PmST2-$His_6$. Positive recombinant plasmid was transformed into E. coli BL21 (DE3) for overexpression. E. coli strain bearing the recombinant plasmid was grown in LB medium supplemented with ampicillin (100 μg $ml^{-1}$) until $OD_{600\ nm}$ of 0.8-1.0 was reached. Overexpression of the protein was achieved by inducing the E. coli culture with 0.1 mM isopropyl-1-thio-β-D-galactopyranoside (IPTG) at 20° C. for 18-20 h. The bacterial cells were harvested by centrifugation at 4° C. in a Sorvall Legend RT centrifuge with a hanging bucket rotor at 3,696×g for 2 h. Harvested cells were resuspended in 20 ml lysis buffer (pH 8.0, Tris-HCl containing 0.1% Triton X-100) for cells collected from one liter cell culture. Lysozyme (100 μg $ml^{-1}$) and DNaseI (5 μg $ml^{-1}$) were added to the cell resuspension. The resulting mixture was then incubated at 37° C. for 1 h with shaking at 210 rpm. Cell lysate (supernatant) was obtained by centrifugation at 14,905×g for 45 min. Purification was carried out by loading the supernatant onto a $Ni^{2+}$-NTA column pre-equilibrated with 10 column volumes of binding buffer (10 mM imidazole, 0.5 M NaCl, 50 mM Tris-HCl, pH 8.0). The column was wash with 10 column volumes of binding buffer and 10 column volumes of washing buffer (50 mM imidazole, 0.5 M NaCl, 50 mM Tris-HCl, pH 8.0). The target protein was eluted with Tris-HCl buffer (50 mM, pH 8.0) containing imidazole (200 mM) and NaCl (0.5 M). The amount of protein obtained was analyzed by BCA method. The fractions containing the purified enzymes were collected and dialyzed against Tris-HCl buffer (20 mM, pH 8.0) containing 10% glycerol. Dialyzed proteins were stored at 4° C.

Sodium Dodecylsulfate-Polyacrylamide Gel Electrophoresis (SDS-PAGE). SDS-PAGE was performed in 12% Tris-glycine gels using Bio-Rad Mini-protein III cell gel electrophoresis unit (Bio-Rad, Hercules, Calif.) at DC=150 V. Bio-Rad Low range SDS-PAGE standards or Precision Plus Protein Standards were used as molecular weight standards. Gels were stained with Coomassie Blue.

Quantification of Purified Protein. Protein concentration was determined in a 96-well plate using a Bicinchoninic acid (BCA) Protein Assay Kit (Pierce Biotechnology, Rockford, Ill.) with bovine serum albumin as a protein standard. The absorbance of each sample was measured at 562 nm on a multiple-well plate reader (BioTek Synergy HT RDR Multitedection Plate Reader).

Protein Encoded by the Pm0508 Gene Homolog from Pm Strain P-1059 (ATCC 15742)

Protein encoded by Pm0508 gene from *Pasteurella multocida*(strain Pm70), designated as PmST2, was identified by BLAST search as a hypothetic sialyltransferase due to its protein sequence homology (31% sequence identity) to a lipooligosaccharide α2,3-sialyltransferase from *Neisseria meningitidis* encoded by 1st gene. DNA sequencing of the cloned Pm0508 gene homolog from Pm strain P-1059 (ATCC15742) indicates that it has four base differences (t74c, c87t, c306t, t867c) compared to the published Pm0508 gene sequence of the genomic strain Pm70, resulting in only one amino acid difference (M25T) in the deduced protein. Amino acid sequence alignment using ClustalW multiple alignment program (FIG. 1) shows the homology shared by protein sequences encoded by the Pm0508 gene homolog, *Haemophilus influenzae* LsgB (40% identity), and *N. meningitidis* Lst (30% identity). Hydropathy plot (TMpred) indicated that there are two possible transmembrane helices in PmST2. One spanned from 1-19 amino acid residues and the other spanned from 85-107 amino acid residues. The first possible transmembrane helix (1-19 aa) is shared among all members of GT52 family and the second transmembrane helix (85-107 aa) is shared among some GT52 family members.

Expression and Purification of MBP-PmST2-$His_6$

Initially, the full-length Pm0508 gene from *Pasteurella multocida* P-1059was cloned into pET22b(+) and expressed as a C-$His_6$ (SEQ ID NO:9) tagged fusion protein. Expression in *E. coli* BL21 (DE3) at 20 ° C. for 20 hrs with vigorous shaking (250 rpm) after induction with isopropyl-1-thio-β-D-galactopyranoside (IPTG, 0.1 mM) yielded ~3 mg of soluble protein that can be purified from cell lysate obtained from one liter cell culture by $Ni^{2+}$-NTA affinity column. The yield of soluble enzyme was improved by introducing an N-terminal maltose binding protein (MBP) to the fusion protein. Under the same expression conditions, active and soluble recombinant protein MBP-PmST2-$His_6$ can be routinely purified at a level of 21 mg from cell lysate obtained from one liter *E. coli* culture by $Ni^{2+}$-NTA affinity column. As shown in FIG. 2, the recombinant protein showed a molecular weight of around 75 kD by SDS-PAGE, which was close to its calculated molecular weight of 79.5 kDa.

Example 2

Time-Course Studies for MBP-PmST2-$His_6$ and PmST1

Methods.

Enzymatic reactions were performed in a total volume of 20 μl (when LacβPro2AA was used as an acceptor) or 40 μl (when LacβPro-triazole-C 14 was used as an acceptor) in a Tris-HCl buffer (200 mM, pH 8.0) containing an acceptor (2 mM of LacβPro2AA or LacβPro-triazole-C14), CMP-Neu5Ac (8 mM), 0.3% Triton X-100, and a sialyltransferase (2.4 MBP-PmST2-$His_6$ or PmST1) at 37° C. At different time points (0, 1, 5, 10, 15, 20, 30, and 60 min), 1.5 μl aliquots were taken from the LacβPro2AA reaction and pre-chilled 12% acetonitrile aqueous solution (148.5 μl) was added to each aliquot. Similarly, 3.5 μl aliquots were taken from the Lacβ-Pro-triazole-C14 reaction at different time points and pre-chilled 95% ethanol (7 μl) was added to each aliquot. All samples were kept on ice for 10 min and then centrifuged for 5 min at 13,000 rpm. Supernatants from LacβPro2AA reactions were analyzed by a Shimadzu LC-2010A HPLC system equipped with a membrane on-line degasser, a temperature control unit, and a fluorescence detector (the excitation wavelength was set at 315 nm and the emission wavelength was set at 400 nm) using a reverse phase Premier C18 column (250×4.6 mm I.D., 5 μm particle size, Shimadzu) protected with a C18 guard column cartridge. Mobile phase used was 12% acetonitrile in water. Supernatants from LacβPro-triazole-C14 reactions were analyzed by a Beckman P/ACE MDQ capillary electrophoresis (CE) system (60 cm×75 μm i.d.) equipped with a PDA detector (optimal absorption at 214 nm). The running buffer used was sodium borate buffer (50 mM, pH 10.2) containing β-cyclcodextrin (20 mM).

Results.

Both LacβPro2AA and LacβPro-triazole-C14 (FIG. 3) were used as acceptor substrates for the time course studies of the sialyltransferase activity of MPB-PmST2-$His_6$ and PmST1. The reactions were carried out under same conditions with the same molar concentrations of enzymes and substrates. As shown in FIG. 4, PmST1 was very active towards LacβPro2AA (FIG. 4A, dashed line with open circles), the sialyltransferase reaction reached optimum at 1 min. The sialidase activity of the PmST1 was then responsible for cleaving the product formed. In comparison, LacβPro-triazole-C14 was not a good acceptor for PmST1 (FIG. 4B, dashed line with open circles). The sialyltransferase reaction reached to an optimum at 15 min with less than 5% product formation. The sialidase activity then started to hydrolyze the product formed. In contrast, LacβPro-triazole-C14 (FIG. 4B, solid line with filled diamonds) was a much better acceptor substrate for MBP-PmST2-$His_6$ than LacβPro2AA (FIG. 4A, solid line with filled diamonds). A 60% yield of sialylation was achieved in 1 hour by MBP-PmST2-$His_6$ when LacβPro-triazole-C14 was used as an acceptor, while only 15% sialylation was achieved in the same time frame when LacβPro2AA was used as an acceptor.

Example 3 pH Profiles of MBP-PmST2-$His_6$

Methods.

Each reaction was carried out in duplicate at 37° C. for 15 min in a buffer (200 mM) with a total volume of 15 μl containing an acceptor (2 mM, LacβPro2AA or LacβPro-triazole-C14), CMP-Neu5Ac (8 mM), 0.3% Triton X-100, and the enzyme MBP-PmST2-$His_6$ (2.4 μg $μl^{-1}$). Buffers used were: NaOAc-HOAc (pH 4.0-6.0), Tris-HCl (pH 7.0-9.0), and CHES (pH 10.0). Enzymatic reactions were terminated by adding 15 μl of pre-chilled 95% ethanol. All samples were kept on ice for 10 min and then centrifuged at 13,000 rpm for 5 min. Supernatants were analyzed by HPLC (for LacβPro2AA reaction) or CE (for LacβPro-triazole-C14 reaction) as described above for the time course studies.

Results.

The pH profile studies were carried out for MBP-PmST2-$His_6$ using either LacβPro2AA (FIG. 5, dashed line with open circles) or LacβPro-triazole-C14 (FIG. 5, solid line with filled diamonds) as the acceptor substrate. The α-2,3-sialyltransferase activity of MBP-PmST2-$His_6$ was active in a broad pH range of 4.5-10.0. The optimal pH was 6.0. When LacβPro2AA was used as the acceptor, pH of the buffer in the range of 4.5 to 9.0 did not change the α2,3-sialyltransferase activity of the enzyme significantly. In comparison, when LacβPro-triazole-C14 was used as the acceptor, the optimal pH range is 5.0-8.0 and the α-2,3-sialyltransferase activity of the enzyme decreased modestly at pH 4.5 and 9.0. Low activity was found at pH 10.0 and no significant activity was found at pH 4.0.

Example 4

Effects of Metal Ions, EDTA, and a Reducing Reagent on MBP-PmST2-His$_6$ Activity Methods.

Reactions were carried out in duplicate at 37° C. for 15 min in a total volume of 15 μl in a Tris-HCl buffer (200 mM, pH 8.0) containing LacβPro-triazole-C14 (2 mM), CMP-Neu5Ac (8 mM), 0.3% Triton X-100, and the enzyme (2.4 μg μl$^{-1}$). For metal effects, various concentrations (1, 5, 10, or 20 mM) of MgCl$_2$ or MnCl$_2$ were added and ethylenediaminetetraacetic acid (EDTA as chelating agent was used at two concentrations (1 or 10 mM). A reducing reagent 2-mercaptoethanol (2-ME) was used at two concentrations (1 or 10 mM). Reaction without metal ions, EDTA, or 2-ME was used as a control. All reactions were stopped by adding 15 μl of pre-chilled 95% ethanol and the reaction mixtures were kept on ice. The samples were centrifuged at 13,000 rpm for 5 min before the supernatants were analyzed by CE as described above.

Results.

Figure 6:
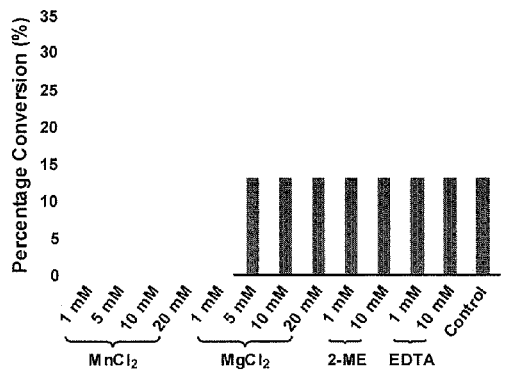
FIG. 6 shows the effects of divalent metal concentrations, EDTA, and 2-mercaptoethanol (2-ME) on the α2,3-sialyltransferase activity of MBP-PmST2-His$_6$ using LacβProtriazole-C14 as the acceptor substrate in the presence of 0.3% of Triton X-100.

Similar to other sialyltransferases reported before, divalent metal cations are not required by the α2,3-sialyltransferase activity of MBP-PmST2-His$_6$ as the addition of different concentrations of MnCl$_2$ or MgCl$_2$ (1, 5, 10 or 20 mM) or EDTA (1 mM or 10 mM) did not affect the activity significantly (26-32% conversions) (FIG. 6). Different from the effect of MnCl$_2$ at high concentration in decreasing the activity of PmST1 and a truncated *Photobacterium damselae* α2,6-sialyltransferase (Pd2,6ST), the presence of MnCl$_2$ at a concentration up to 20 mM did not decrease the activity of PmST2. Although MBP-PmST2-His$_6$ has six cysteine residues in the PmST2 protein sequence and among which three cysteine residues near the N-terminus are highly conserved among homologous bacterial sialyltransferases, the addition of a reducing reagent 2-mercaptoethanol at 1 mM or 10 mM did not affect the α2,3-sialyltransferase activity of MBP-PmST2-His$_6$. This indicates that disulfide bonds are not required for the enzymatic activity.

Example 5

Kinetic Studies

Methods.

Reactions were carried out at 37° C. for 10 mM in a total volume of 15 μl in Tris-HCl buffer (200 mM, pH 8.0) containing 2-mercaptoethanol (1 mM), 0.3% Triton X-100, enzyme (14 μM), with varied CMP-Neu5Ac concentrations (0.25, 0.5, 1.0, 2.0, 5.0, and 10.0 mM) and a fixed LacβPro-triazole-C14 (2.0 mM) concentration, or varied LacβPro-triazole-C14 concentrations (0.5, 1.0, 2.0, 5.0, 10.0, and 20.0 mM) or varied LacβPro2AA concentrations (0.5, 1.0, 2.0, 5.0, 10.0, and 25.0 mM) and a fixed CMP-Neu5Ac concentration (4.0 mM). HPLC assays were used for reactions with LacβPro2AA as the sialyltransferase acceptor and CE assays were used for reactions with LacβPro-triazole-C14 as the sialyltransferase acceptor. Apparent kinetic parameters were obtained by fitting the data (the average values of duplicate assay results) into the Michaelis-Menten equation using Grafit 5.0.

Results.

As shown in Table 1, the binding of MBP-PmST2-His$_6$ to a β-lactoside with a long hydrocarbon chain (LacβPro-triazole-C14, $K_M$=4.1±0.3 mM) was stronger (7-fold difference in $K_M$ values) than its binding to a lactoside without the long hydrocarbon chain (LacβPro2AA, $K_M$=28±3 mM). In addition, the turn over number was higher when LacβPro-triazole-C14 ($k_{cat}$=12±1 min$^{-1}$) was used as the acceptor for the α2,3-sialyltransferase activity of MBP-PmST2-His$_6$ compared to LacβPro2AA ($k_{cat}$=7.9±0.7 min$^{-1}$) as the acceptor. The differences in both $K_M$ and $k_{cat}$ lead to a 10-fold higher catalytic activity when LacβPro-triazole-C14 was used as the acceptor substrate.

TABLE 1

Apparent kinetic parameters for the α-2,3-sialyltransferase activity of MBP-PmST2-His$_6$.

| Substrates | CMP-Neu5Ac | LacβPro-triazole-C14 | LacβPro2AA |
|---|---|---|---|
| $K_M$ (mM) | 1.3 ± 0.1 | 4.1 ± 0.3 | 28 ± 3 |
| $V_{max}$ (mM min$^{-1}$) | (7.4 ± 0.5) × 10$^{-2}$ | (1.7 ± 0.1) × 10$^{-1}$ | (1.1 ± 0.1) × 10$^{-1}$ |
| $k_{cat}$ (min$^{-1}$) | 5.3 ± 0.4 | 12 ± 1 | 7.9 ± 0.7 |
| $k_{cat}/K_M$ (min$^{-1}$ mM$^{-1}$) | 4.1 | 2.9 | 0.28 |

Example 6

Enzymatic Synthesis of Characterization of Sialosides

Methods

Neu5Acα2-3LacβPro-triazole-C14. LacβPro-triazole-C14 (34 mg, 0.052 mmol), N-acetylneuraminic acid (Neu5Ac) (24 mg, 0.079 mmol), CTP (44 mg, 0.079 mmol), and MgCl$_2$ (43 mg, 21 mM) were dissolved in 10 ml of Tris-HCl buffer (100 mM, pH 8.5, 1 ml). After the addition of *N. meningitidis* CMP-sialic acid synthetase (NmCSS, 1.4 mg) and MBP-PmST2-His$_6$ (5.8 mg), the reaction was carried out by incubating the solution in an incubator shaker overnight at 37° C. The reaction was then quenched by adding cold EtOH (10 ml) and the mixture was centrifuged to remove the precipitates. The filtrate was concentrated and purified by a BioGel P-2 filtration column (elute with water) and a silica gel column (EtOAc:MeOH:H$_2$O, 7:2:1) to afford Neu5Acα2-3LacβPro-triazole-C14 (36 mg, 73%).

Sialyl lactosyl sphingosine (lyso-GM3). Lactosyl sphingosine (15 mg, 0.026 mmol), Neu5Ac (12 mg, 0.039 mmol), CTP (22 mg, 0.039 mmol), and MgCl$_2$ (22 mg, 22 mM) were dissolved in 5 ml of Tris-HCl buffer (100 mM, pH 8.5) in the presence of 0.2% Triton X-100. After the addition of NmCSS (0.8 mg) and MBP-PmST2-His$_6$ (2.9 mg), the reaction was carried out by incubating the solution in an incubator shaker overnight at 37° C. The reaction was then quenched by adding cold EtOH (5 ml) and the mixture was centrifuged to remove the precipitates. The filtrate was concentrated and purified by a BioGel P-2 filtration column (elute with water) and a silica gel column (EtOAc:MeOH:H$_2$O=6:2:1 by volume) to afford Neu5Acα2-3Lactosyl sphingosine (15 mg, 68%).

Results.

Figure 7:
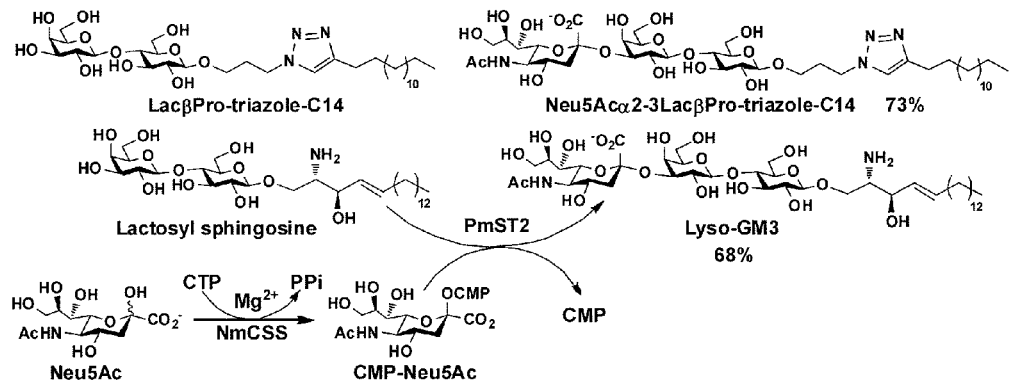
FIG. 7 shows a schematic diagram for the one-pot, two-enzyme synthesis of lyso-GM3 from lactosyl sphingosine and CTP using a recombinant *N. meningitidis* CMP-sialic acid synthetase (NmCSS) and PmST2 in the presence of Mg$^{2+}$.

Preparative enzymatic synthesis of α2,3-linked sialosides Neu5Acα2-3LacβPro-triazole-C14 and Neu5Acα2-3lactosyl sphingosine (lyso-GM3) using a one-pot two-enzyme system containing a recombinant *N. meningitidis* CMP-sialic acid synthetase (NmCSS) and MBP-PmST2-His$_6$ (FIG. 7)

led to 73% and 68% yields, respectively. Nuclear magnetic resonance (NMR) and high-resolution mass spectrometry (ESI-HRMS) studies confirmed the structures of both sialosides Neu5Acα2-3LacβPro-triazole-C14 and Lyso-GM3. The α-2,3-sialyl linkage formed in Neu5Acα2-3LacβPro-triazole-C14 was determined by comparing the chemical shift values of the product and the acceptor LacβPro-triazole-C14. As shown in Table 2, a significant downfield shift on the C3 of the Gal in the sialoside products compared to LacβPro-triazole-C14 (72.66 ppm in the acceptor compared to 77.76 ppm in the product) and lactosyl sphingosine (72.64 ppm in the acceptor compared to 77.84 ppm in the product) acceptors and small upfield chemical shifts on the neighboring C2 indicated that the sialylation occurred at the C3 of the Gal in the acceptors. High resolution mass spectrometry (HRMS) spectra obtained using electrospray ionization (ESI) method showed the desired m/z for molecular ions. For Neu5Acα2-3LacβPro-triazole-C14, the m/z (937.4845) matched well to the calculated m/z value (937.4874) for $C_{42}H_{73}N_4O_{19}$ (M-H). For Lyso-GM3, the m/z (913.4726) matched well to the calculated value (913.4762) for $C_{41}H_{73}N_2O_{20}$ (M-H).

Example 7

Acceptor Substrate Specificity Studies of MBP-PmST2-$His_6$

Methods.

General Synthetic Methods. Chemicals were purchased and used without further purification. $^1$H NMR (600 MHz) and $^{13}$C NMR (150 MHz) spectra were recorded on a Varian VNMRS 600 MHz spectrometer for Lacβ2AA. All other $^1$H and $^{13}$C NMR spectra were recorded on a Bruker 800 MHz spectrometer. High resolution electrospray ionization (ESI) mass spectra were obtained at the Mass Spectrometry Facility in the University of California, Davis. Silica gel 60 Å was used for flash column chromatography. Thin-layer chromatography (TLC) was performed on silica gel plates using anisaldehyde sugar stain or 5% sulfuric acid in ethanol stain for detection. Gel filtration chromatography was performed with a column (100 cm×2.5 cm) packed with BioGel P-2 Fine resins. *N. meningitidis* CMP-sialic acid synthetase (NmCSS) was expressed in *E. coli* and purified as described previously.

TABLE 2

$^{13}$C NMR chemical shifts assignement of LacβPro-triazole-C14, Neu5Acα2-3LacβPro-triazole-C14, Lactosyl sphingosine, and Lyso-GM3.

| | | Chemical shift (ppm) | | | |
|---|---|---|---|---|---|
| Residue | Carbon atom | LacβPro-triazole-C14 | Neu5Acα2-3LacβPro-triazole-C14 | Lactosyl sphingosine | Lyso-GM3 |
| βDGlc | C | | | | |
| | 1 | 104.34 | 104.36 | 104.34 | 104.00 |
| | 2 | 74.90 | 74.84 | 74.80 | 74.67 |
| | 3 | 74.97 | 75.05 | 74.91 | 75.10 |
| | 4 | 77.19 | 77.17 | 77.19 | 77.26 |
| | 5 | 76.51 | 76.45 | 76.37 | 76.38 |
| | 6 | 62.07 | 62.05 | 61.92 | 62.00 |
| βDGal(1-4) | 1 | 105.26 | 105.22 | 105.21 | 105.30 |
| | 2 | 74.87 | 73.95 | 74.73 | 73.96 |
| | 3 | 72.66 | 77.76 | 72.64 | 77.84 |
| | 4 | 70.46 | 70.22 | 70.39 | 70.35 |
| | 5 | 76.63 | 76.60 | 76.60 | 76.38 |
| | 6 | 62.63 | 62.83 | 62.59 | 62.87 |
| αDNeu5Ac(2-3) | 1 | | 175.02 | | 174.91 |
| | 2 | | 101.25 | | 101.22 |
| | 3 | | 42.21 | | 42.33 |
| | 4 | | 69.10 | | 69.12 |
| | 5 | | 54.08 | | 54.13 |
| | 6 | | 73.07 | | 73.08 |
| | 7 | | 69.46 | | 69.44 |
| | 8 | | 70.94 | | 70.92 |
| | 9 | | 61.80 | | 61.89 |
| | C=O | | 175.59 | | 175.64 |
| | $CH_3$ | | 22.69 | | 22.68 |
| Pro-triazole-C14 | O$\underline{C}$H$_2$CH$_2$CH$_2$(N$_3$CH=C)CH$_2$CH$_2$(CH$_2$)$_{10}$CH$_2$CH$_3$ | 67.13 | 67.02 | | |
| | OCH$_2$$\underline{C}$H$_2$CH$_2$(N$_3$CH=C)CH$_2$CH$_2$(CH$_2$)$_{10}$CH$_2$CH$_3$ | 26.38 | 26.37 | | |
| | OCH$_2$CH$_2$$\underline{C}$H$_2$(N$_3$CH=C)CH$_2$CH$_2$(CH$_2$)$_{10}$CH$_2$CH$_3$ | 48.19 | 48.16 | | |
| | OCH$_2$CH$_2$CH$_2$(N$_3$$\underline{C}$H=C)CH$_2$CH$_2$(CH$_2$)$_{10}$CH$_2$CH$_3$ | 123.75 | 123.86 | | |
| | OCH$_2$CH$_2$CH$_2$(N$_3$CH=$\underline{C}$)CH$_2$CH$_2$(CH$_2$)$_{10}$CH$_2$CH$_3$ | 149.34 | 149.26 | | |
| | OCH$_2$CH$_2$CH$_2$(N$_3$CH=C)$\underline{C}$H$_2$CH$_2$(CH$_2$)$_{10}$CH$_2$CH$_3$ | 33.11 | 33.15 | | |
| | OCH$_2$CH$_2$CH$_2$(N$_3$CH=C)CH$_2$$\underline{C}$H$_2$(CH$_2$)$_{10}$CH$_2$CH$_3$ | 31.61 | 31.62 | | |
| | OCH$_2$CH$_2$CH$_2$(N$_3$CH=C)CH$_2$CH$_2$($\underline{C}$H$_2$)$_{10}$CH$_2$CH$_3$ | 30.32-30.79 | 30.35-30.84 | | |
| | OCH$_2$CH$_2$CH$_2$(N$_3$CH=C)CH$_2$CH$_2$(CH$_2$)$_{10}$$\underline{C}$H$_2$CH$_3$ | 23.76 | 23.81 | | |
| | OCH$_2$CH$_2$CH$_2$(N$_3$CH=C)CH$_2$CH$_2$(CH$_2$)$_{10}$CH$_2$$\underline{C}$H$_3$ | 14.46 | 14.52 | | |
| Sphingosine | O$\underline{C}$H$_2$CHNH$_2$CHOHCH=CHCH$_2$CH$_2$(CH$_2$)$_9$CH$_2$CH$_3$ | | | 71.73 | 71.61 |
| | OCH$_2$$\underline{C}$HNH$_2$CHOHCH=CHCH$_2$CH$_2$(CH$_2$)$_9$CH$_2$CH$_3$ | | | 56.30 | 56.87 |
| | OCH$_2$CHNH$_2$$\underline{C}$HOHCH=CHCH$_2$CH$_2$(CH$_2$)$_9$CH$_2$CH$_3$ | | | 80.61 | 80.92 |
| | OCH$_2$CHNH$_2$CHOH$\underline{C}$H=CHCH$_2$CH$_2$(CH$_2$)$_9$CH$_2$CH$_3$ | | | 135.79 | 136.68 |
| | OCH$_2$CHNH$_2$CHOHCH=$\underline{C}$HCH$_2$CH$_2$(CH$_2$)$_9$CH$_2$CH$_3$ | | | 130.92 | 128.76 |
| | OCH$_2$CHNH$_2$CHOHCH=CH$\underline{C}$H$_2$CH$_2$(CH$_2$)$_9$CH$_2$CH$_3$ | | | 33.54 | 33.44 |
| | OCH$_2$CHNH$_2$CHOHCH=CHCH$_2$$\underline{C}$H$_2$(CH$_2$)$_9$CH$_2$CH$_3$ | | | 33.18 | 33.12 |
| | OCH$_2$CHNH$_2$CHOHCH=CHCH$_2$CH$_2$($\underline{C}$H$_2$)$_9$CH$_2$CH$_3$ | | | 30.47-30.90 | 30.28-30.83 |
| | OCH$_2$CHNH$_2$CHOHCH=CHCH$_2$CH$_2$(CH$_2$)$_9$$\underline{C}$H$_2$CH$_3$ | | | 23.84 | 23.78 |
| | OCH$_2$CHNH$_2$CHOHCH=CHCH$_2$CH$_2$(CH$_2$)$_9$CH$_2$$\underline{C}$H$_3$ | | | 14.55 | 14.48 |

Figure 8:
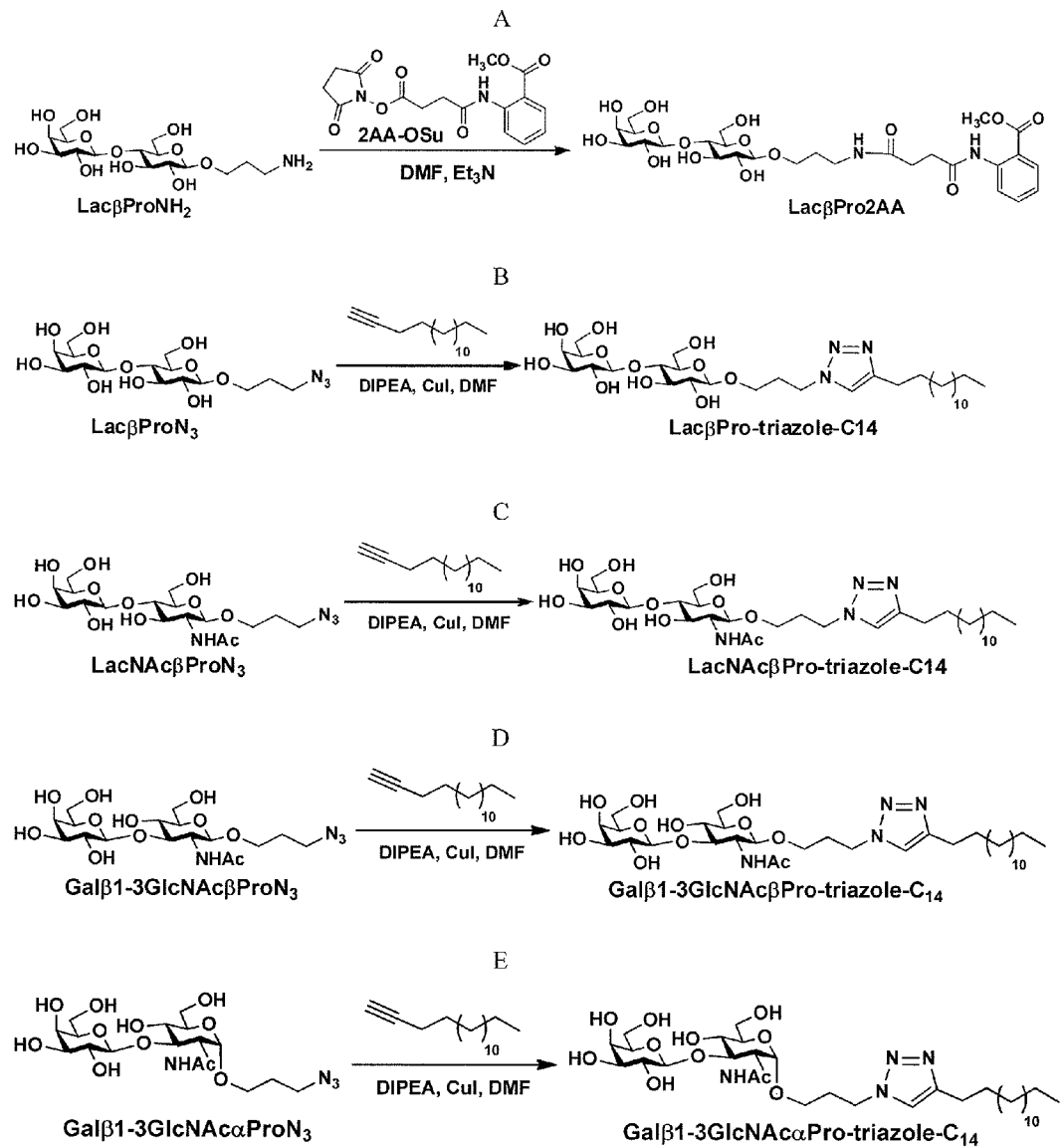
FIG. 8 shows schematic diagrams for the chemical synthesis of various PmST2 acceptor substrates.

Synthesis of LacβPro2AA. LacβPro2AA was prepared according to FIG. 8A. To a solution of LacβProNH$_2$ (30 mg, 0.075 mmol) in 6 ml anhydrous DMF, dry triethylamine (50 μl) was added under argon atmosphere. Two equivalents of N-hydroxy succinamide (NHS) activated 4-((2-(methoxycarbonyl)phenyl)amino)-4-oxobutanoic acid (2AA-OSu) (52 mg, 0.15 mmol) were then added at 0° C. The resulted solution was stirred at room temperature for overnight. The reaction mixture was concentrated and the residue was purified by flash column chromatography (EtOAc:MeOH:H$_2$O=9:2:1 by volume) to afford pure LacβPro2AA (40 mg, 84%). $^1$H NMR (600 MHz, D$_2$O): δ 8.01 (d, 1H, J=7.8 Hz), 7.88 (d, 1H, J=8.4 Hz), 7.67 (t, 1H, J=7.8 Hz), 7.35 (t, 1H, J=7.8 Hz), 4.45 (d, 1H, J=7.8 Hz), 4.37 (d, 1H, J=8.4 Hz), 3.96-3.55 (m, 15H), 3.51-3.49 (m, 1H), 3.35-3.29 (m, 3H), 2.79 (t, 2H, J=6.6 Hz), 2.64 (t, 2H, J=6.6 Hz), 1.82 (m, 2H); $^{13}$C NMR (150 MHz, D$_2$O): δ 174.66, 173.63, 169.27, 137.24, 134.16, 131.07, 125.50, 123.63, 121.05, 103.11, 102.23, 78.59, 75.52, 74.88, 74.52, 72.96, 72.73, 71.12, 68.71, 67.83, 61.18, 60.24, 52.95, 36.35, 32.54, 31.17, 28.55. HRMS (ESI) m/z calcd for C$_{27}$H$_{40}$N$_2$O$_{15}$Na (M-Na) 655.2326. Found 655.2352.

Synthesis of LacβPro-triazole-C14. LacβPro-triazole-C14 was synthesized according to FIG. 8B. To a solution of Lacβ-ProN$_3$ (80 mg, 0.19 mmol) in 10 ml anhydrous DMF, hexadecyne (126 mg, 0.57 mmol) and DIPEA (74 mg, 0.57 mmol) were added. CuI (25 mg, 0.13 mmol) was then added into the reaction mixture and the resulted solution was stirred at room temperature for overnight. The reaction mixture was concentrated and the residue was purified by flash column chromatography (EtOAc:MeOH:H$_2$O, 12:2:1) to afford pure Lacβ-Pro-triazole-C14 (76 mg, 62%). The detailed NMR data is shown in Table 2. HRMS (ESI) m/z calcd for C$_{31}$H$_{57}$N$_3$O$_{11}$Na (M-Na) 670.3891. Found 670.3904.

Synthesis of LacNAcβPro-triazole-C14. LacNAcβPro-triazole-C14 was synthesize according to FIG. 8c. To a solution of LacNAcβProN$_3$(30 mg, 0.064 mmol) in 5 ml anhydrous MeOH, hexadecyne (72 mg, 0.32 mmol) and DIPEA (25 mg, 0.19 mmol) were added. CuI (12 mg, 0.062 mmol) was then added into the reaction mixture and the resulted solution was stirred at room temperature for 2 days. The reaction mixture was concentrated and the residue was purified by flash column chromatography (EtOAc:MeOH:H$_2$O, 12:2:1) to afford pure LacNAcβPro-triazole-C14 (35 mg, 78%). $^1$H NMR (800 MHz, MeOD) δ 7.83 (s, 1H), 4.58-4.56 (m, 2H), 4.53 (d, J=8 Hz, 1H), 4.50 (d, J=8 Hz, 1H), 4.01-3.94 (m, 4H), 3.89-3.87 (m, 2H), 3.82 (dd, J=4.8 and 11.2 Hz, 1H), 3.76-3.70 (m, 3H), 3.67-3.52 (m, 4H), 2.78 (t, J=8 Hz, 2H), 2.24-2.19 (m, 2H), 2.11 (s, 3H), 1.78-1.76 (m, 2H), 1.45-1.39 (m, 22), 1.00 (t, J=7.2 Hz, 3H) $^{13}$C HMR (200 MHz, MeOD) δ 171.27, 147.83, 121.93, 103.65, 101.32, 79.48, 75.66, 75.10, 73.36, 72.81, 71.12, 68.93, 65.32, 61.10, 60.44, 55.23, 46.50, 31.56, 30.01, 29.23-38.77 (10C), 24.82, 22.21, 21.61, 12.91. HRMS (ESI) m/z calculated for C$_{17}$H$_{31}$N$_4$O$_{11}$ (M+H) 467.1989, measured 467.1988. HRMS (ESI) m/z calcd for C$_{33}$H$_{60}$N$_4$O$_{11}$Na (M-Na) 711.4156. Found 711.4141.

Synthesis of Galβ1-3GlcNAcβPro-triazole-C14. Galβ1-3GlcNAcβPro-triazole-C14 was prepared according to FIG. 8D. To the solution of Galβ1-3GlcNAcβProN$_3$ (40 mg, 0.086 mmol) in 5 ml anhydrous MeOH, hexadecyne (95 mg, 0.43 mmol) and DIPEA (33 mg, 0.26 mmol) were added. CuI (17 mg, 0.088 mmol) was then added into the reaction mixture and the resulted solution was stirred at room temperature for 2 days. The reaction mixture was concentrated and the residue was purified by flash column chromatography (EtOAc:MeOH:H$_2$O, 12:2:1) to afford pure Galβ1-3GlcNAcβPro-triazole-C14 (44 mg, 74%). $^1$H NMR (800 MHz, MeOD) δ 7.84 (s, 1H), 4.60 (d, J=8.8 Hz, 1H), 4.58-4.52 (m, 2H), 4.43 (d, J=8 Hz, 1H), 4.00-3.86 (m, 5H), 3.83-3.80 (m, 3H), 3.70-3.60 (m, 4H), 3.54 (t, J=8.8 Hz, 1H), 3.45-3.43 (m, 1H), 2.78 (t, J=8 Hz, 2H), 2.24-2.20 (m, 2H), 2.12 (s, 3H), 1.78-1.75 (m, 2H), 1.45-1.39 (m, 22), 1.00 (t, J=7.2 Hz, 3H) $^{13}$C HMR (200 MHz, MeOH) δ 172.91, 147.85, 121.96, 104.08, 101.00, 76.13, 75.60, 73.19, 70.91, 69.08, 68.82, 68.80, 65.37, 61.21, 61.02, 57.77, 46.54, 31.56, 30.02, 29.27-28.78 (10C), 24.83, 22.22, 21.83, 12.93. HRMS (ESI) m/z calcd for C$_{33}$H$_{60}$N$_4$O$_{11}$Na (M-Na) 711.4156. Found 711.4142.

Synthesis of Galβ1-3GlcNAcαPro-triazole-C14. Galβ1-3GlcNAcαPro-triazole-C14 was prepared according to FIG. 8E. To the solution of Galβ1-3GlcNAcαProN$_3$(50 mg, 0.11 mmol) in 5 ml anhydrous MeOH, hexadecyne (119 mg, 0.54 mmol) and DIPEA (42 mg, 0.32 mmol) were added. CuI (21 mg, 0.11 mmol) was then added into the reaction mixture and the resulted solution was stirred at room temperature for 2 days. The reaction mixture was concentrated and the residue was purified by flash column chromatography (EtOAc:MeOH:H$_2$O, 12:2:1) to afford pure Galβ1-3GlcNAcαPro-triazole-C14 (53 mg, 71%). $^1$H NMR (800 MHz, MeOD) δ 7.91 (s, 1H), 4.87 (d, J=3.2 Hz, 1H), 4.72-4.63 (m, 2H), 4.58 (d, J=6.4 Hz, 1H), 4.21 (dd, J=3.2 Hz and 10.4 Hz, 1H), 3.98-3.82 (m, 7H), 3.76-3.73 (m, 2H), 3.65-3.64 (m, 2H), 3.58 (t, J=9.6 Hz, 1H), 3.48-3.45 (m, 1H), 2.79 (t, J=7.2 Hz, 2H), 2.34-2.30 (m, 2H), 2.15 (s, 3H), 1.78-1.76 (m, 2H), 1.45-1.39 (m, 22), 1.00 (t, J=7.2 Hz, 3H) $^{13}$C HMR (200 MHz, MeOD) δ 172.82, 147.93, 121.90, 103.69, 97.51, 75.51, 73.18, 72.25, 70.95, 69.04, 68.92, 68.89, 63.97, 61.10, 61.04, 52.62, 46.81, 31.59, 29.74, 29.29-28.39 (10C), 24.87, 22.26, 21.62, 13.00. HRMS (ESI) m/z calcd for C$_{33}$H$_{60}$N$_4$O$_{11}$Na (M-Na) 711.4156. Found 711.4141.

Synthesis of Galβ1-3GalNAcαPro-triazole-C14. Galβ1-3GalNAcαPro-triazole-C14 was prepared according to FIG. 8F. To a solution of Galβ1-3GalNAcαProN$_3$ (30 mg, 0.064 mmol) in 5 ml anhydrous MeOH, hexadecyne (72 mg, 0.32 mmol) and DIPEA (25 mg, 0.19 mmol) were added. CuI (12 mg, 0.062 mmol) was then added into the reaction mixture and the resulted solution was stirred at room temperature for 2 days. The reaction mixture was concentrated and the residue was purified by flash column chromatography (EtOAc:MeOH:H$_2$O, 12:2:1) to afford pure Galβ1-3GalNAcαPro-triazole-C14 (31 mg, 69%). $^1$H NMR (800 MHz, MeOD) δ 7.87 (s, 1H), 4.92 (d, J=4 Hz, 1H), 4.69-4.61 (m, 2H), 4.57 (d, J=8 Hz, 1H), 4.53 (dd, J=3.2 Hz and 10.4 Hz, 1H), 4.29 (m, 1H), 4.03 (dd, J=2.4 Hz and 10.4 Hz, 1H), 3.96 (m, 2H), 3.88-3.82 (m, 5H), 3.68-3.60 (m, 3H), 3.48-3.46 (m, 1H), 2.79 (t, J=7.2 Hz, 2H), 2.34-2.28 (m, 2H), 2.13 (s, 3H), 1.78-1.76 (m, 2H), 1.45-1.39 (m, 22), 1.00 (t, J=7.2 Hz, 3H) $^{13}$C HMR (200 MHz, MeOD) δ 172.70, 147.00, 121.76, 104.74, 97.74, 77.56, 75.25, 73.28, 71.12, 70.69, 68.95, 68.73, 64.03, 61.46, 61.16, 48.76, 46.82, 31.56, 29.74, 29.26-28.77 (10C), 24.85, 22.21, 21.52, 12.92. HRMS (ESI) m/z calcd for C$_{33}$H$_{60}$N$_4$O$_{11}$Na (M-Na) 711.4156. Found 711.4154.

Synthesis of GalβPro-triazole-C14. GalβPro-triazole-C14 was synthesized according to FIG. 8G. To the solution of GalβProN$_3$ (30 mg, 0.11 mmol) in 5 ml anhydrous MeOH, hexadecyne (127 mg, 0.57 mmol) and DIPEA (44 mg, 0.34 mmol) were added. CuI (22 mg, 0.11 mmol) was then added into the reaction mixture and the resulted solution was stirred at room temperature for 2 days. The reaction mixture was concentrated and the residue was purified by flash column chromatography (EtOAc:MeOH, 13:2) to afford pure Galβ-Pro-triazole-C 14 (35 mg, 64%). NMR (800 MHz, MeOD) δ 7.89 (s, 1H), 4.64-4.62 (m, 2H), 4.32 (d, J=7.2 Hz, 1H), 4.01-3.98 (m, 1H), 3.95 (d, J=2.4 Hz, 1H), 3.87-3.83 (m, 2H), 3.66-3.58 (m, 4H), 2.78 (t, J=7.2 Hz, 2H), 2.28-2.27 (m, 2H), 1.78-1.76 (m, 2H), 1.45-1.39 (m, 22), 1.00 (t, J=7.2 Hz, 3H). $^{13}$C HMR (200 MHz, MeOD) δ 172.70, 147.71, 122.26, 103.57, 75.25, 73.55, 71.11, 68.87, 61.08, 46.59, 31.56, 30.09, 29.24-27.86 (10C), 24.82, 22.22, 12.91. HRMS (ESI) m/z calcd for $C_{25}H_{47}N_3O_6Na$ (M-Na) 508.3363. Found 508.3342.

Enzymatic Reactions. All reactions were carried out in duplicate for 10 min at 37° C. in a total volume of 10 μl in Tris-HCl (200 mM, pH 8.0) containing an acceptor substrate (2 mM), CMP-Neu5Ac (4 mM), 0.4% Triton X-100, and enzyme (3.6 μg μl$^{-1}$). Addition of 15 μl of cold 95% ethanol was used to terminate each reaction. All reactions were incubated on ice for 10 min and were then centrifuged for 5 min at 13,000 rpm. The supernatant was transferred to a new vial for CE analysis.

Results.

To test the acceptor substrate specificity of MBP-PmST2-His$_6$, a list of glycosides containing a long hydrocarbon tail (Pro-triazole-C14) including Galβ1-4GlcNAcβPro-triazole-C14 (LacNAcβPro-triazole-C14), Galβ1-3GlcNAcβPro-triazole-C14, Galβ1-3GlcNAcαPro-triazole-C14, Galβ1-3GalNAcαPro-triazole-C14, and GalβPro-triazole-C14 in addition to Galβ1-4Glcβ Pro-triazole-C14 (LacβPro-triazole-C14) were chemically synthesized and used as potential acceptors for PmST2. As shown in Table 3, β1-4-linked galactosides such as LacNAcβPro-triazole-C14 and Lacβ-Pro-triazole-C14 were better acceptor substrates for PmST2 than β1-3-linked galactosides such as Galβ1-3GlcNAcβPro-triazole-C14 (lacto-N-biose or LNB-type structure), Galβ1-3GlcNAcαPro-triazole-C14, Galβ1-3GalNAcαPro-triazole-C14 (galacto-N-biose or GNB-type structure). In addition, the β-galactosylmonosaccharide lipid was a worse PmST2 acceptor than β1-4-linked galactosyldisaccharide lipids but a better acceptor than β1-3-linked galactosyldisaccharide lipids. While GNB is generally found in mucin-type O-GalNAc glycans representing one of the core antigens (core 1 or T antigen), LNB is a well-known component of human milk oligosaccharides, glycoproteins or glycolipids. On the other hand, LacNAc and Lac are commonly presented as the glycan components of bacterial glycolipids such as in *Neisseria* and *Haemophilus*. Among all Pro-triazole-C14-containing galactosides tested, LacβPro-triazole-C14 was the best acceptor substrate for PmST2. This means that the natural acceptor of PmST2 may resembles lactosyl lipid the best. Commercially available lactosyl ceramide was also tested but was found not an acceptor for PmST2.

TABLE 3

Acceptor substrate specificity of MBP-PmST2-His$_6$.

| Acceptor Substrate | % product formation$^a$ | % Relative$^b$ |
|---|---|---|
| LacβPro-triazole-C14 | 36.1 ± 1.5 | 100 |
| LacNAcβPro-triazole-C14 | 18.5 ± 2.7 | 51.2 |
| GalβPro-triazole-C14 | 9.2 ± 1.3 | 25.5 |
| Galβ1-3GlcNAcβPro-triazole-C14 (LNBβ) | <4 | <11 |
| Galβ1-3GlcNAcαPro-triazole-C14 (LNBα) | <2 | <6 |
| Galβ1-3GalNAcαPro-triazole-C14 (GNBα) | <2 | <6 |

All sialyltransferases identified to date have been classified into six glycosyltransferase families GT4, GT29, GT38, GT42, GT52, and GT80 by the Carbohydrate-Active enZymes (CAZy) (http://www.cazy.org/) database based on protein sequence homology. All eukaryotic sialyltransferases and some viral sialyltransferases have been grouped into GT29. Polysialyltransferase (SiaD) from *Neisseria meningitidis* W135 responsible for the synthesis of capsular polysaccharide belongs to GT4 along with other glycosyltransferases, while α-2,8-polysialyltransferases from *E. coli* (NeuS) and *N meningitides* serogroup B strains (SiaD) are grouped into GT38. GT42 includes α-2,3-sialyltransferases (CstI and CstIII) from *Campylobacter jejuni*, as well as multifunctional α2,3/8-sialyltransferases from *Campylobacter jejuni* (CstII) or *Haemophilus influenzae* (Lic3B). An 2,3-sialyltransferase encoded by *Haemophilus influenzae* lic3A gene and a hypothetical sialyltransferase encoded by *Pasteurella multocida* Pm1174 gene are also grouped into this GT42 family. Unlike PmST1 encoded by Pm0188 gene analog which belongs to CAZy GT80 family containing multifunctional bacterial α2,3- and or α-2,6-sialyltransferases, PmST2 encoded by Pm0508 gene analog belongs to CAZy GT52 family. This GT52 family also contains characterized α-2,3/6-sialyltransferases from *Neisseria meningitides* (Lst), *Neisseria gonorrhoeae* (Lst), *Haemophilus influenzae* (LsgB), as well as a *Salmonella enterica* α1,2-glucosyltransferase (WaaH). CpsK, another member of GT52 family and a homolog to the Lst of *Haemophilus ducreyi*, has also been identified as a putative α2,3-sialylatransferase for the synthesis of sialic acid-terminated capsular polysaccharide of *Streptococcus agalactiae* (GBS or Group B *Streptococcus*).

PmST2encoded by gene Pm0508 is in the midst of a locus (Pm0506 to Pm0512) of putative glycosyltransferases. It lines up very well with the so-called lipooligosaccharide synthesis genes (lsg) locus from both *H. influenzae* and *H. ducreyi*. Here we demonstrate that PmST2, the Lst from *Pasteurella multocida* encoded by Pm0508 gene analog, is a novel α2,3-sialyltransferase that can be used for synthesizing sialylglycolipids. Therefore, two of the three potential sialyltransferase gene products of *Pasteurella multocida* strain Pm70 have now been confirmed to be functional sialyltransferases.

Although sialylated capsular polysaccharide or lipooligosaccharide (LOS) structures have yet been reported for *Pasteurella multocida*, it appears that *Pasteurella multocida* has invested significantly for sialic acid metabolism and has been shown to be able to use sialic acid as the sole carbon source. Two sialidases, one sialic acid aldolase/lyase (encoded by gene Pm1715), at least one CMP-sialic acid synthetase (encoded by gene Pm0187) (gene Pm1710 may also encode another putative CMP-sialic acid synthetase), and a possible tripartite ATP-dependent periplasmic (TRAP) sialic acid transporter have been identified in Pm. Furthermore, membrane-associated sialyltransferase activity has been detected in multiple Pm strains and a relatively low molecular weight product resembling LOS may be the possible native acceptor. Sialylation of cell surface oligosaccharides has also been demonstrated vital for the virulence of *Pasteurella multocida*. Nevertheless, sialylated structures have not been isolated from *Pasteurella multocida* yet. Therefore, the natural acceptor for PmST2 is currently unknown. Our substrate specificity studies of PmST2 showed that LacβPro-triazole-C14 was the best acceptor among all galactosyl lipids tested. This indicate that the natural acceptor substrate of PmST2 may resembles lactosyl lipid. Two possible transmembrane helices have been identified in PmST2 by hydropathy plot (TMpred). The first one spanning from 1-19 amino acid residues is conserved among all members of GT52 family and the second one spanning from 85-107 amino acid residues has only been found in some GT52 family members. It has yet to be determined whether one of these transmembrane helices or both are involved in the binding to the lipid portion of the glycosyl lipid substrates.

It seems that the presence of multiple sialyltransferase genes is a common feature for members of the *Haemophilus-Actinobacillus-Pasteurella* (HAP). For example, four sialyltransferase genes (siaA, lic3A, lic3B, and lsgB) have been identified in *H influenzae*. While Lic3A is an α2,3-sialyltransferase in all *H influenzae* strains, Lic3B has been confirmed to be a bifunctional α2,3/8-sialyltransferase which only exist in some of the *H influenzae* strains. *Haemophilus ducreyi* 35000HP has at least two functional sialyltransferases and at least two functional sialyltransferases have now been confirmed in *Pasteurella multocida*.

Compared with *H. influenzae* (an obligate human microparasite), Pm has a broader host range and has continued to cause a wide range of diseases in animals and humans. Nevertheless, similar to that described for other HAP members such as *H. influenzae, H. ducreyi*, and *H. somnus, Pasteurella multocida* seems to acquire sialic acids from the environment or the host through the precursor scavenging sialylation mechanism since it lacks the genes for early steps of de novo sialic acid synthesis. This precursor scavenging pathway could be a common sialylation mechanism for the HAP group.

A previous report indicates that *N. meningitidis* (MC58 and 406Y) Lst has no stringent metal requirement although the activity can be stimulated by $Mg^{2+}$(2-fold) or $Mn^{2+}$(3-fold). Similarly, metal ions are not required for PmST2 and the addition of either $MnCl_2$ or $MgCl_2$ does not affect the sialyltransferase activity of PmST2 significantly. In comparison, although the α2-3-sialyltransferase activity of PmST1 does not require metal ions and the addition of $Mg^{2+}$ does not stimulate or change the sialyltransferase activity, the activity decreases with the addition of $Mn^{2+}$. Unlike PmST1 which has multiple functions such as α2,3-sialyltransferase, α2,6-sialyltransferase, α2,3-sialidase, and α2,3-trans-sialidase activities, PmST2 seems to be monofunctional α2,3-sialyltransferase without sialidase activity. This monofunctionality of PmST2 allows efficient synthesis of glycolipids without worrying about product hydrolysis. PmST2 has been used successfully in preparative scale synthesis of sialyllactosyl sphingosine (lyso-GM3). PmST2 thus joins a list of bacterial and mammalian α2,3-sialyltransferases including *Neisseria meningitidis* α2,3-sialyltransferase, *Campylobacter jejuni*α2,3-sialyltransferase, porcine submaxillary gland α2,3-sialyltransferase, porcine liver α2,3-sialyltransferase, recombinant rat liver Galβ1-4GlcNAcα2-3-(N)-sialyltransferase, and several sialyltransferases from marine bacteria for efficient synthesis of lyso-GM3 and its derivatives, which are themselves important probes while can also be used as intermediates for synthesizing more complex gangliosides. With a good expression level in *E. coli* and the superior α2,3-sialyltransferase activity using lactosyl lipids including lactosyl sphingosine as acceptors, PmST2 is an efficient catalyst for large scale chemoenzymatic synthesis of α2,3-linked sialylglycolipids for elucidating their important biological functions.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of preparing a glycolipid product, the method comprising:
   forming a reaction mixture comprising an acceptor glycolipid, a donor substrate comprising a sugar moiety and a nucleotide, and a polypeptide selected from the group consisting of:
   SEQ ID NO:4 (PmST2),
   SEQ ID NO:5 (PmST2-His$_6$), and
   SEQ ID NO:6 (MBP-PmST2-His$_6$),
   wherein the reaction mixture is formed under conditions sufficient to transfer the sugar moiety from the donor substrate to the acceptor glycolipid, thereby forming the glycolipid product.

2. The method of claim 1, wherein the acceptor glycolipid comprises a galactoside moiety.

3. The method of claim 2, wherein the galactoside moiety is selected from the group consisting of a β1-4 linked galactoside moiety and a β1-3 linked galactoside moiety.

4. The method of claim 2, wherein the acceptor glycolipid comprises a lactoside moiety or an N-acetyl lactosaminide moiety.

5. The method of claim 2, wherein the acceptor glycolipid comprises a Galβ1-3GlcNAc moiety or a Galβ1-3GalNAc moiety.

6. The method of claim 1, wherein the donor substrate comprises a cytidine 5'-monophosphate (CMP)-sialic acid.

7. The method of claim 6, wherein the CMP-sialic acid comprises cytidine 5'-monophosphate N-acetylneuraminic acid (CMP-Neu5Ac) or a CMP-Neu5Ac analog.

8. The method of claim 7, wherein the CMP-Neu5Ac or CMP- Neu5Ac analong is prepared prepared by a process comprising forming a reaction mixture comprising a CMP-sialic acid synthetase, cytidine triphosphate, and N-acetylneuraminic acid (Neu5Ac) or a Neu5Ac analog under conditions sufficient to form the CMP-Neu5Ac or CMP-Neu5Ac analog.

9. The method of claim 8, wherein preparing the CMP-Neu5Ac or CMP- Neu5Ac analong and preparing the glycolipid product are performed in one pot.

10. The method of claim 8, wherein the Neu b5c or Neu5analog is prepared by a process comprising forming a reaction mixture comprising a sialic acid aldolase, pyruvic acid or derivatives thereof, and N-acetylmannosamine or derivatives thereof under conditions sufficient to form the Neu5Ac or Neu5Ac analog.

11. The method of claim 10, wherein preparing the Neu5Ac or Neu5Ac anlalog, preparing the CMP-Neu5c or CMP-Neu5Ac analog, and preparing the glycolipid product are performed in one pot.

12. The method of any of claims 1-11, wherein the glycolipid product is an α-2,3-linked sialylglycolipid.

13. The method of claim 12, wherein the α-2,3-linked sialylglycolipid is Neu5Acα2-3lactosyl sphingosine (lyso-GM3) or a derivative thereof.

* * * * *

UNITED STATES PATENT AND TRADEMARK OFFICE
CERTIFICATE OF CORRECTION

PATENT NO. : 9,102,967 B2
APPLICATION NO. : 13/739705
DATED : August 11, 2015
INVENTOR(S) : Xi Chen et al.

It is certified that error appears in the above-identified patent and that said Letters Patent is hereby corrected as shown below:

IN THE CLAIMS

In claim 8, line 14, please delete "CMP- Neu5Ac analong" and insert --CMP-Neu5Ac analog--.

In claim 9, line 2, please delete "CMP- Neu5Ac analong" and insert --CMP-Neu5Ac analog--.

In claim 10, line 4, please delete "Neu b5c" and insert --Neu5Ac--.

In claim 10, line 5, please delete "Neu5analog" and insert --Neu5Ac analog--.

In claim 11, line 11, please delete "Neu5Ac anlalog, preparing the CMP-Neu5c" and insert --Neu5Ac analog, preparing the CMP-Neu5Ac--.

Signed and Sealed this
Fifteenth Day of March, 2016

Michelle K. Lee
*Director of the United States Patent and Trademark Office*